US012409209B2

(12) United States Patent
Koizumi et al.

(10) Patent No.: US 12,409,209 B2
(45) Date of Patent: Sep. 9, 2025

(54) BIOLOGICAL FUNCTION REGULATING AGENT, EPIDERMAL METABOLISM PROMOTING AGENT, FAT ACCUMULATION INHIBITING AGENT, FAT DECOMPOSITION PROMOTING AGENT, ADIPONECTIN PRODUCTION PROMOTING AGENT, FUNCTIONAL FOOD, COSMETIC PRODUCT, AND METHOD FOR PRODUCING BIOLOGICAL FUNCTION REGULATING AGENT

(71) Applicant: NITTA GELATIN INC., Osaka (JP)

(72) Inventors: Seiko Koizumi, Yao (JP); Mona Sato, Yao (JP); Ai Himeno, Yao (JP); Toshirou Watanabe, Amagasaki (JP)

(73) Assignee: NITTA GELATIN INC., Osaka (JP)

( * ) Notice: Subject to any disclaimer, the term of this patent is extended or adjusted under 35 U.S.C. 154(b) by 516 days.

(21) Appl. No.: 17/917,391

(22) PCT Filed: Mar. 22, 2021

(86) PCT No.: PCT/JP2021/011586
§ 371 (c)(1),
(2) Date: Oct. 6, 2022

(87) PCT Pub. No.: WO2021/205852
PCT Pub. Date: Oct. 14, 2021

(65) Prior Publication Data
US 2023/0158121 A1 May 25, 2023

(30) Foreign Application Priority Data
Apr. 7, 2020 (JP) .................................. 2020-069230

(51) Int. Cl.
*A61K 38/39* (2006.01)
*A61K 47/08* (2006.01)
*A61K 47/10* (2017.01)
*A61P 3/04* (2006.01)

(52) U.S. Cl.
CPC .............. *A61K 38/39* (2013.01); *A61K 47/08* (2013.01); *A61K 47/10* (2013.01); *A61P 3/04* (2018.01)

(58) Field of Classification Search
CPC ........ A61K 38/39; A61K 47/08; A61K 47/10; A61P 3/04
See application file for complete search history.

(56) References Cited

FOREIGN PATENT DOCUMENTS

| CN | 101709319 A | 5/2010 |
|---|---|---|
| CN | 104041804 A | 9/2014 |
| CN | 104105414 A | 10/2014 |
| CN | 105255972 A | 1/2016 |
| CN | 105861565 A | 8/2016 |
| JP | 2010-178736 A | 8/2010 |
| JP | 2012-87091 A | 5/2012 |
| JP | 2013-124222 A | 6/2013 |
| JP | 2018-023326 A | 2/2018 |
| KR | 10-2012-0079964 A | 7/2012 |
| WO | 2017/014149 A1 | 1/2017 |
| WO | 2019/131274 A1 | 7/2019 |

OTHER PUBLICATIONS

Communication issued Oct. 23, 2024 in Japanese Application No. 110110869.
Minji Woo et al., "Anti-Obesity Effects of Collagen Peptide Derived from Skate (*Raja kenojei*) Skin Through Regulation of Lipid Metabolism", Marine Drugs, 2018, pp. 1-12, vol. 16 (9), 306.
Hatsumi Kobayashi et al., "Change in Hepatic Gene Expression and Anti-Obesity Effects by Oral Ingestion of Salmon Skin Collagen Peptide", Proceedings of 2012 Annual Meeting of The Japanese Society for Food Science and Technology, Aug. 29, 2012, vol. 59th, p. 97.
"Unknown Possibilities for Fermented Collagen" section, "High Skin Moisturizing Effect" section, non-official translation (with "Collagen x Fermentation", "Penetrating Fermentation Collagen", Open a New Era for Collagen. Dr. Ci:Labo Develops worls's First Stably Combined Skincare Cosmetic, 4 pages, [Online] Feb. 16, 2018, [retrived on May 2021], <URL: https://prtimes.jp/a/?c=2961 &r=242&f=d2961-242-pdf-0.pdf >, Press release file at (URL: https://prtimes.jp/main/html/rd/p/000000242.000002961.html.
Mie Takahashi et al., "GC-Olfactometry analysis of the aroma components in sake koji", J. Brew. Soc. Japan, 2006, pp. 957-963, vol. 101, No. 12.
International Search Report for PCT/JP2021/011586, dated May 25, 2021.
Wu Hai-Bin et al., "The Optimization of Fermentation Cod Fish Skin with *Aspergillus oryzae* to Produce Peptides of LMW and the Research of Bioactivity of Fermentation Peptides", Food and Fermentation Industries, vol. 37, No. 5, May 31, 2011, pp. 110-114.
Communication dated Sep. 23, 2024, issued in Chinese application No. 202180026971.1.
Youn-Soo Cha et al., "Visceral fat and body weight are reduced in overweight adults by the supplementation of *Doenjang*, a fermented soybean paste", Nutrition Research and Practice, 2012, vol. 6, No. 6, pp. 520-526.
Yunzi Feng et al., "Effect of koji fermentation on generation of volatile compounds in soy sauce production", International Journal of Food Science and Technology 2013, vol. 48, pp. 609-619.
Yoshihiko Sugihara et al., "Improvement of skin conditions by ingestion of *Aspergillus kawachii* (Koji) extract containing 14-dehydroergosterol in a randomized, double-blind, controlled trial", Clinical, Cosmetic and Investigational Dermatology, 2018, vol. 11, pp. 115-124.

(Continued)

*Primary Examiner* — Amber D Steele
(74) *Attorney, Agent, or Firm* — Sughrue Mion, PLLC

(57) ABSTRACT

A biological function regulating agent comprises a fermented collagen peptide, and the fermented collagen peptide has at least one action selected from the group consisting of an epidermal metabolism promoting action, a fat accumulation inhibiting action, a fat decomposition promoting action and an action of regulating the amount of adipocytokine in a biological body.

11 Claims, 8 Drawing Sheets

(56) References Cited

OTHER PUBLICATIONS

"Development and market trends of protein and peptide materials, food processing and ingredients", 2000, vol. 35, No. 8, pp. 18-23 (8 pages total).
"Lookout, Food and Science", 2008, vol. 50, No. 5, pp. 16-23 (10 pages total).
Office Action issued Apr. 8, 2025 in Japanese Application No. 2022-514374.
Chinese Office Action dated May 26, 2025 in Application No. 202180026971.1.

DIFFERENT ALPHABETS INDICATE
A SIGNIFICANT DIFFERENCE(P<0.05)

DIFFERENT ALPHABETS INDICATE
A SIGNIFICANT DIFFERENCE(P<0.05)

※ DIFFERENT ALPHABETS (LOWER CASE LETTERS) INDICATE A SIGNIFICANT DIFFERENCE(P<0.05)

※ DIFFERENT ALPHABETS (LOWER CASE LETTERS) INDICATE A SIGNIFICANT DIFFERENCE(P<0.05)

※ DIFFERENT ALPHABETS (LOWER CASE LETTERS) INDICATE A SIGNIFICANT DIFFERENCE($p<0.05$)

※ DIFFERENT ALPHABETS (LOWER CASE LETTERS) INDICATE A SIGNIFICANT DIFFERENCE($p<0.05$)

※ DIFFERENT ALPHABETS (LOWER CASE LETTERS) INDICATE A SIGNIFICANT DIFFERENCE($p<0.05$)

※ DIFFERENT ALPHABETS (LOWER CASE LETTERS) INDICATE A SIGNIFICANT DIFFERENCE($P<0.05$)

※ DIFFERENT ALPHABETS (LOWER CASE LETTERS) INDICATE A SIGNIFICANT DIFFERENCE($P<0.05$)

※ DIFFERENT ALPHABETS (LOWER CASE LETTERS) INDICATE A SIGNIFICANT DIFFERENCE($P<0.05$)

BIOLOGICAL FUNCTION REGULATING AGENT, EPIDERMAL METABOLISM PROMOTING AGENT, FAT ACCUMULATION INHIBITING AGENT, FAT DECOMPOSITION PROMOTING AGENT, ADIPONECTIN PRODUCTION PROMOTING AGENT, FUNCTIONAL FOOD, COSMETIC PRODUCT, AND METHOD FOR PRODUCING BIOLOGICAL FUNCTION REGULATING AGENT

CROSS REFERENCE TO RELATED APPLICATIONS

This application is a National Stage of International Application No. PCT/JP2021/011586 filed Mar. 22, 2021, claiming priority based on Patent Japanese Application No. 2020-069230 filed Apr. 7, 2020.

TECHNICAL FIELD

The present invention relates to a biological function regulating agent, an epidermal metabolism promoting agent, a fat accumulation inhibiting agent, a fat decomposition promoting agent, an adiponectin production promoting agent, a functional food, a cosmetic product, and a method for producing a biological function regulating agent.

BACKGROUND ART

WO 2017/014149 (Patent Literature 1), a paper submitted by Woo et al. (Non Patent Literature 1), and a publication presented by Kobayashi et al. (Non Patent Literature 2) state that a collagen peptide has an anti-obesity action. Japanese Patent Laying-Open No. 2018-023326 (Patent Literature 2) discloses that a collagen peptide was obtained by fermenting collagen with lactic acid bacteria.

CITATION LIST

Patent Literature

PTL 1: WO 2017/014149
PTL 2: Japanese Patent Laying-Open No. 2018-023326

Non Patent Literature

NPL 1: M Woo et al., "Anti-Obesity Effects of Collagen Peptide Derived from Skate (Raja kenojei) Skin Through Regulation of Lipid Metabolism", Marine Drugs, 2018, Vol. 16 (9), 306
NPL 2: Kobayashi et al., "Change in Hepatic Gene Expression and Anti-Obesity Effects by Oral Ingestion of Salmon Skin Collagen Peptide", Proceedings of 2012 Annual Meeting of The Japanese Society for Food Science and Technology, 29 Aug. 2012, Vol. 59th Page. 97

SUMMARY OF INVENTION

Technical Problem

Patent Literature 2 does not disclose that a collagen peptide is obtained by fermenting any of collagen, gelatin and gelatin degradation products with koji. Further, the collagen peptide having been reported to have an anti-obesity action in Patent Literature 1, Non Patent Literature 1 and Non Patent Literature 2 is not a collagen peptide obtained by fermenting any of collagen, gelatin and gelatin degradation products with koji (hereinafter, also referred to as a "fermented collagen peptide"). That is, the effects of a fermented collagen peptide on a biological body have not been clarified yet.

In view of the circumstances described above, an object of the present invention is to provide a biological function regulating agent comprising a fermented collagen peptide having at least one action selected from the group consisting of an epidermal metabolism promoting action, a fat accumulation inhibiting action, a fat decomposition promoting action and an action of regulating the amount of adipocytokine in a biological body, an epidermal metabolism promoting agent, a fat accumulation inhibiting agent, a fat decomposition promoting agent, an adiponectin production promoting agent, a functional food, a cosmetic product, and a method for producing a biological function regulating agent.

Solution to Problem

The present inventors have found that a fermented collagen peptide obtained by fermenting any of raw materials containing collagen, such as hide, skin, bone, cartilage and tendon of a quadruped and bone, skin and scale of fish, collagen, gelatin and gelatin degradation products with koji has at least one action selected from the group consisting of an epidermal metabolism promoting action, a fat accumulation inhibiting action, a fat decomposition promoting action and an action of regulating the amount of adipocytokine in a biological body, and thus completed the present invention.

Specifically, the present invention has characteristics as described below.

[1] The biological function regulating agent according to the present invention comprises a fermented collagen peptide, the fermented collagen peptide having at least one action selected from the group consisting of an epidermal metabolism promoting action, a fat accumulation inhibiting action, a fat decomposition promoting action and an action of regulating the amount of adipocytokine in a biological body.
[2] It is preferable that the fermented collagen peptide comprise a collagen peptide, and at least one first compound selected from the group consisting of isovaleric aldehyde, 1-octen-3-ol, phenylacetaldehyde and methional.
[3] It is preferable that the fermented collagen peptide comprise a collagen peptide, and at least three first compounds selected from the group consisting of isovaleric aldehyde, 1-octen-3-ol, phenylacetaldehyde and methional.
[4] The epidermal metabolism promoting agent according to the present invention comprises the biological function regulating agent.
[5] The fat accumulation inhibiting agent according to the present invention comprises the biological function regulating agent.
[6] The adiponectin production promoting agent according to the present invention comprises the biological function regulating agent.
[7] The fat decomposition promoting agent according to the present invention comprises the biological function regulating agent.
[8] The functional food according to the present invention comprises the biological function regulating agent.
[9] The cosmetic product according to the present invention comprises the biological function regulating agent.
[10] The method for producing a biological function regulating agent according to the present invention is a method for producing a biological function regulating agent comprising a fermented collagen peptide, the method comprising: providing koji containing koji mold, and a collagen raw material; and fermenting the collagen raw material with the koji to obtain a biological function regulating agent comprising the fermented collagen peptide, wherein the bacterial type of the koji mold is a bacterial type belonging to *Aspergillus*, and the collagen raw material is at least any of at least one selected from the group consisting of the following first to sixth groups, collagen extracted from at least one selected from the group, gelatin obtained by treating the collagen, and a gelatin degradation product obtained by hydrolyzing the gelatin:

First group: group consisting of hide, skin, bone, cartilage and tendon of cattle;
Second group: group consisting of hide, skin, bone, cartilage and tendon of pig;
Third group: group consisting of hide, skin, bone, cartilage and tendon of sheep;
Fourth group: group consisting of hide, skin, bone, cartilage and tendon of chicken;
Fifth group: group consisting of hide, skin, bone, cartilage and tendon of ostrich;
Sixth group: group consisting of bone, skin and scale of fish.

[11] The biological function regulating agent according to the present invention comprises a fermented collagen peptide produced by fermenting a collagen raw material with koji.

Advantageous Effects of Invention

According to the above, it is possible to provide a biological function regulating agent comprising a fermented collagen peptide having at least one action selected from the group consisting of an epidermal metabolism promoting action, a fat accumulation inhibiting action, a fat decomposition promoting action and an action of regulating the amount of adipocytokine in a biological body, an epidermal metabolism promoting agent, a fat accumulation inhibiting agent, a fat decomposition promoting agent, an adiponectin production promoting agent, a functional food, a cosmetic product, and a method for producing a biological function regulating agent.

DESCRIPTION OF EMBODIMENTS

Figure 1:
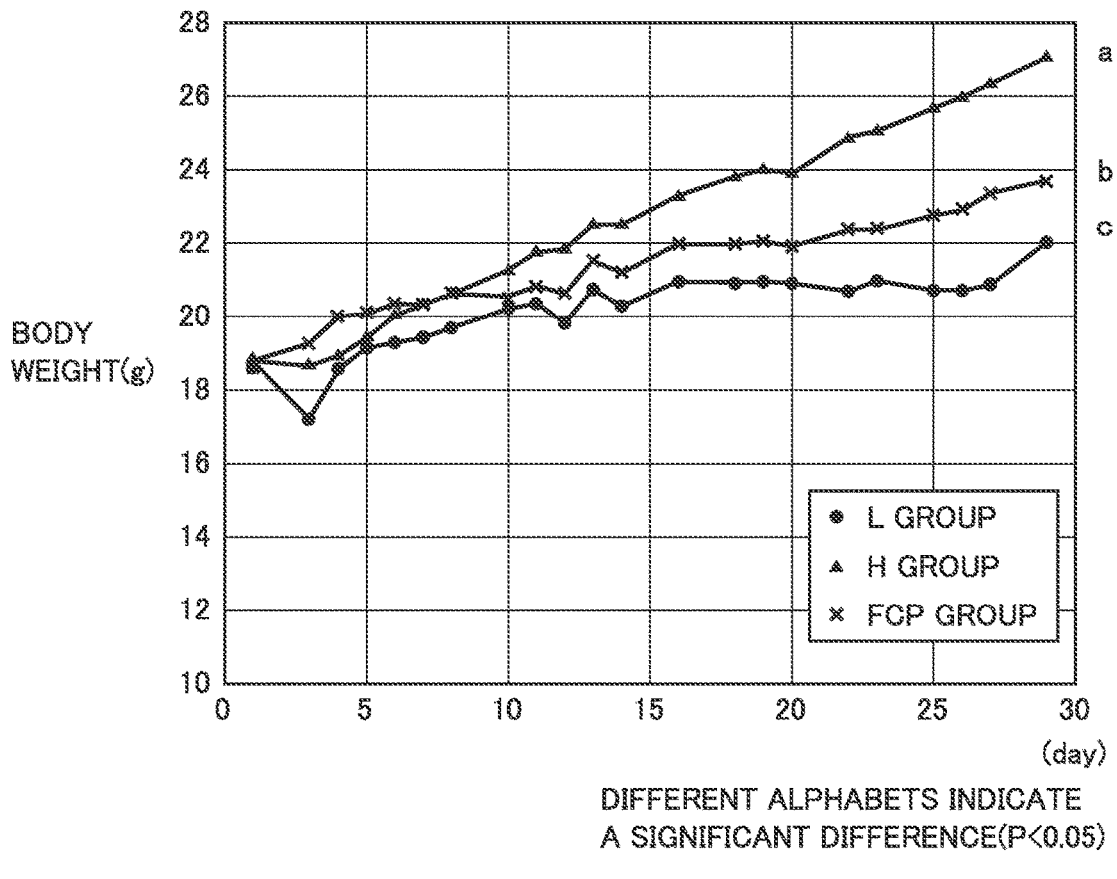
FIG. 1 is a graph showing changes in body weight of the mice of the groups in the first test.

Hereinafter, embodiments according to the present invention (hereinafter, also referred to as "the present embodiment") will be described in more detail. Here, as used herein, the wording "A to B" means the upper limit and the lower limit of a range (i.e. A or more and B or less), and when a unit is not described for A, but described only for B, the unit for A is identical to the unit for B.

As used herein, the "biological function regulating agent", "epidermal metabolism promoting agent", "fat accumulation inhibiting agent", "fat decomposition promoting agent", "adiponectin production promoting agent" and "fermented collagen peptide" may be in the form of a solid such as powder, or a liquid such as an aqueous solution obtained by dissolution in water. Further, as used herein, the term "fermented collagen peptide" means a peptide mixture obtained by fermenting a collagen raw material described later with koji. As used herein, the term "fermentation" means the entirety of a process of generation of a useful organic substance from a raw material by activity of koji mold contained in koji, and is distinguished from "rot" in which an organic substance that is not useful is generated from a raw material by activity of microorganisms.

As used herein, the term "gelatin" may be used when any of a substance name, a gelatin gel and a gelatin solution is mentioned. As in the case of the gelatin, the term "collagen peptide" may be used when any of a substance name and a collagen peptide solution is mentioned.

As used herein, the term "collagen raw material" may be used when at least one "itself" selected from the group consisting of the following first to sixth groups, "collagen" extracted from at least one selected from the group consisting of the following first to sixth groups, "gelatin" obtained by treating the collagen using a known method such as hot water extraction, and a "gelatin degradation product" obtained by hydrolyzing the gelatin are collectively mentioned. Further, the "hydrolysis" of the gelatin includes all of hydrolysis with an acid, hydrolysis with a base, hydrolysis with an enzyme and hydrolysis by heating.

First group: group consisting of hide, skin, bone, cartilage and tendon of cattle
Second group: group consisting of hide, skin, bone, cartilage and tendon of pig
Third group: group consisting of hide, skin, bone, cartilage and tendon of sheep
Fourth group: group consisting of hide, skin, bone, cartilage and tendon of chicken
Fifth group: group consisting of hide, skin, bone, cartilage and tendon of ostrich
Sixth group: group consisting of bone, skin and scale of fish.

Biological Function Regulating Agent

The biological function regulating agent according to the present embodiment comprises a fermented collagen peptide. The fermented collagen peptide has at least one action selected from the group consisting of an epidermal metabolism promoting action, a fat accumulation inhibiting action, a fat decomposition promoting action and an action of regulating the amount of adipocytokine in a biological body. The biological function regulating agent having such a characteristic can exert on a biological body at least one action selected from the group consisting of an epidermal metabolism promoting action, a fat accumulation inhibiting action, a fat decomposition promoting action and an action of regulating the amount of adipocytokine in a biological body (hereinafter, also referred to as a "biological function regulating action").

Fermented Collagen Peptide

The biological function regulating agent according to the present embodiment comprises a fermented collagen peptide as described above. It is preferable that the fermented collagen peptide comprise a collagen peptide, and at least one first compound selected from the group consisting of isovaleric aldehyde, 1-octen-3-ol, phenylacetaldehyde and methional. More preferably, the fermented collagen peptide comprises a collagen peptide, and at least three first compounds selected from the group consisting of isovaleric aldehyde, 1-octen-3-ol, phenylacetaldehyde and methional. This enables more sufficient exertion on a biological body of at least one biological function regulating action selected from the group consisting of an epidermal metabolism promoting action, a fat accumulation inhibiting action, a fat decomposition promoting action and an action of regulating the amount of adipocytokine in a biological body. As described later, the biological function regulating agent according to the present embodiment is produced by fermenting a collagen raw material with koji. That is, the biological function regulating agent according to the present embodiment is a biological function regulating agent comprising a fermented collagen peptide.

Here, in the fermented collagen peptide, a smell of a conventional collagen peptide (so called a collagen smell) is suppressed by the first compound. Thus, with simplified deodorization treatment etc. or without performing deodorization treatment etc., the biological function regulating agent can be used in, for example, an epidermal metabolism promoting agent, a fat accumulation inhibiting agent, a fat decomposition promoting agent, an adiponectin production promoting agent, a functional food and a cosmetic product described later.

Collagen Peptide

It is preferable that the fermented collagen peptide comprise a collagen peptide as described above. This collagen peptide is identical in appearance to a conventionally known collagen peptide. As a peptide mixture in appearance, the collagen peptide contained in the fermented collagen peptide may comprise various peptides such as dipeptides, tripeptides, oligopeptides and polypeptides obtained by performing conventionally known treatment on collagen or gelatin. It is to be noted that a fermented collagen peptide is obtained by fermenting a collagen raw material with koji as described above. Thus, the collagen peptide contained in the fermented collagen peptide is obtained by fermenting a collagen raw material with koji, and produced along with a first compound described later.

Weight-Average Molecular Weight

The collagen peptide contained in the fermented collagen peptide preferably has a weight-average molecular weight of 20000 or less. When the weight-average molecular weight of the collagen peptide is 20000 or less, the biological function regulating agent can be easily applied to the applications of an epidermal metabolism promoting agents, a fat accumulation inhibiting agent, a fat decomposition promoting agent, an adiponectin production promoting agent, a functional food and a cosmetic product without performing additional treatment. The collagen peptide more preferably has a weight-average molecular weight of 10000 or less, still more preferably 6000 or less. The lower limit value of the weight-average molecular weight of the collagen peptide is 76. When the weight-average molecular weight of the collagen peptide is in the above-described range, the biological function regulating agent can sufficiently exert the above-described actions on a biological body in the applications of an epidermal metabolism promoting agent, a fat accumulation inhibiting agent, a fat decomposition promoting agent, an adiponectin production promoting agent, a functional food and a cosmetic product.

The weight-average molecular weight of the collagen peptide contained in the biological function regulating agent can be determined by carrying out size exclusion chromatography (SEC) under the following measurement conditions. The present inventors have confirmed that this measurement method is appropriate even for measurement of a molecular weight exceeding 12000.

Equipment: High performance liquid chromatograph (HPLC) (TOSOH CORPORATION)
Column: TSKGel (registered trademark) G2000 SW$_{XL}$
Column temperature: 40° C.
Eluent: 45 mass % acetonitrile (containing 0.1 mass % TFA)
Flow rate: 1.0 mL/min
Injection amount: 10 µL
Detection: UV 214 nm
Molecular weight marker: The following five types are used.
Cytochrom C Mw: 12000
Aprotinin Mw: 6500
Bacitracin Mw: 1450
Gly-Gly-Tyr-Arg Mw: 451
Gly-Gly-Gly Mw: 189

First Compound

The fermented collagen peptide comprises preferably at least one first compound, more preferably at least three first compounds selected from the group consisting of isovaleric aldehyde, 1-octen-3-ol, phenylacetaldehyde and methional. In the fermented collagen peptide, it is considered that the first compound may be produced along with a collagen peptide by fermenting a collagen raw material with koji. The first compound can function as a marker which indicates that the fermented collagen peptide is obtained by fermenting a collagen raw material with koji.

The fermented collagen peptide may contain any of one first compound selected from isovaleric aldehyde, 1-octen-3-ol, phenylacetaldehyde and methional as the first compound. The fermented collagen peptide may contain isovaleric aldehyde and 1-octen-3-ol, may contain isovaleric aldehyde and phenylacetaldehyde, may contain isovaleric aldehyde and methional, may contain 1-octen-3-ol and phenylacetaldehyde, may contain 1-octen-3-ol and methional, or may contain phenylacetaldehyde and methional as the first compound.

The fermented collagen peptide may contain, as the first compound, isovaleric aldehyde, 1-octen-3-ol and phenylacetaldehyde, may contain isovaleric aldehyde, 1-octen-3-ol and methional, may contain isovaleric aldehyde, phenylacetaldehyde and methional or may contain 1-octen-3-ol, phenylacetaldehyde and methional. The fermented collagen peptide may contain four first compounds (isovaleric aldehyde, 1-octen-3-ol, phenylacetaldehyde and methional). In these cases, the biological function regulating agent can more sufficiently exert on a biological body at least one action selected from the group consisting of an epidermal metabolism promoting action, a fat accumulation inhibiting action, a fat decomposition promoting action and an action of regulating the amount of adipocytokine in a biological body.

Isovaleric Aldehyde

Isovaleric aldehyde is a compound that is also referred to as isovaleric acid aldehyde, 3-methylbutanol or 3-methylbutylaldehyde, and the compound has been conventionally used as a flavor (food additive) or the like.

1-Octen-3-ol

1-Octen-3-ol is a type of unsaturated alcohol, and the compound has been conventionally known to be a component that contributes to the fragrance of matsutake mushroom.

Phenylacetaldehyde

Phenylacetaldehyde is a type of aromatic aldehyde, and the compound has been conventionally used as a formulation raw material for fragrances and flavors, etc.

Methional

Methional is a type of organosulfur compound, and the compound is also referred to as 3-methylthio-1-propanol. Methional is a compound that has been conventionally known to be contained in soy sauce. Further, methional is known to have an action of weakening the fishy odor of meat and fish.

Content

It is preferable that the first compound be contained in the biological function regulating agent at 0.05 ppm or more as a total amount thereof (a total of at least one or more compounds). That is, it is preferable that the biological function regulating agent contain the first compound at 0.05 ppm or more. Further, it is more preferable that the first compound be contained in the biological function regulating agent at 0.4 ppm or more. That is, it is more preferable that the biological function regulating agent contain the first compound at 0.4 ppm or more. The lower limit value of the content of the first compound in the biological function regulating agent is not particularly limited, and it is preferable that the first compound be contained at 0.01 ppm or more as a total amount thereof. The upper limit of the content of the first compound is not particularly limited, and it is preferable that the first compound be contained at 5 ppm or less as a total amount thereof.

Qualitative determination and quantitative determination of the first compound contained in the biological function regulating agent can be performed in the following procedure. First, dry powder of the biological function regulating agent is obtained by a production method described later. Further, 0.5 g of the dry powder is dissolved in 4.5 mL of RO water to obtain a measurement sample. Subsequently, the measurement sample is put in gas chromatography mass spectrometers (trade name: "7890 A GC System" manufactured by Agilent Technologies, Inc. and trade name: "JMS-Q1050 GC" manufactured by JEOL Ltd.), vaporized, and then moved into a column of the analyzer with ultrahigh-purity helium as a carrier gas to separate components contained in the measurement sample by compounds. Further, the compound is detected with a detector of the analyzer. Qualitative determination of the first compound can be performed by comparing data obtained from the detector (spectral data) with standard data. Quantitative determination of the first compound can also be performed on the basis of the spectral data (peak area) obtained from the detector.

Epidermal Metabolism Promoting Agent

The epidermal metabolism promoting agent according to the present embodiment comprises the biological function regulating agent. By the epidermal metabolism promoting action of the biological function regulating agent, the epidermal metabolism promoting agent can induce melanin granules on, for example, a skin surface (in epidermis) to discharge from the skin surface without being retained as pigmentation, freckles and the like. Specifically, the epidermal metabolism promoting agent can increase the expression level of at least one gene selected from the group consisting of transglutaminase 1 (TGM 1), involucrin (Ivl) and keratin 10 (KRT 10). These genes are known to contribute to mature differentiation of layers (keratinous layer, granular layer, prickle cell layer and basal layer) forming the epidermis. Thus, it is considered that metabolism at the epidermis (so called turnover) is promoted due to the above-described increased expression of genes. Further, a skin moisturizing effect, skin wrinkle preventing and/or wrinkle improving effects, and the like may be obtained due to promotion of metabolism at the epidermis.

The concentration of the biological function regulating agent in the epidermal metabolism promoting agent may be 0.01 to 100 mass %. The concentration of the biological function regulating agent in the epidermal metabolism promoting agent means the concentration of a collagen peptide in the biological function regulating agent because the content of the first compound is very small. Thus, the concentration of the biological function regulating agent in the epidermal metabolism promoting agent can be determined by a conventionally known method for measuring the concentration of a collagen peptide. For example, the concentration of the biological function regulating agent in the epidermal metabolism promoting agent can be determined by measuring the percentage by mass of hydroxyproline in a collagen peptide using a chloramine-T method. It is also possible to determine the concentration of the biological function regulating agent in the epidermal metabolism promoting agent by measuring the percentage by mass of hydroxyproline in a collagen peptide using an amino acid analyzer.

Fat Accumulation Inhibiting Agent

The fat accumulation inhibiting agent according to the present embodiment comprises the biological function regulating agent. By the fat accumulation inhibiting action of the biological function regulating agent, the fat accumulation inhibiting agent can exhibit an effect of inhibiting accumulation of fat in the liver, the intestinal tract, the kidney, the testicle and the like (so called visceral fat). Under an action of the biological function regulating agent, i.e. an action of regulating the amount of adipocytokine in a biological body, the fat accumulation inhibiting agent can exhibit a fat accumulation inhibiting effect through an action of reducing the blood concentration of leptin known as an appetite suppressor hormone and an action of increasing the blood concentration of adiponectin which is known to be inversely proportional to the amount of visceral fat in the body. The leptin and the adiponectin are known as proteins classified as adipocytokine secreted from fat cells. That is, the adiponectin production promoting agent according to the present embodiment comprises the biological function regulating agent.

The concentration of the biological function regulating agent in the fat accumulation inhibiting agent may be 0.01 to 100 mass %. The concentration of the biological function regulating agent in the adiponectin production promoting agent can also be 0.01 to 100 mass %. The concentration of the biological function regulating agent in the fat accumulation inhibiting agent and the adiponectin production promoting agent means the concentration of a collagen peptide in the biological function regulating agent because the content of the first compound is very small. Thus, the concentration of the biological function regulating agent in the fat accumulation inhibiting agent and the adiponectin production promoting agent can be determined by a method identical to the above-described method for measuring the concentration of the biological function regulating agent in the epidermal metabolism promoting agent.

Fat Decomposition Promoting Agent

The fat decomposition promoting agent according to the present embodiment comprises the biological function regulating agent. By the fat decomposition promoting action of the biological function regulating agent, the fat decomposition promoting agent can exhibit an effect of promoting decomposition of fat in the liver, the intestinal tract, the kidney, the testicle and the like (so called visceral fat). The concentration of the biological function regulating agent in the fat decomposition promoting agent may be 0.01 to 100 mass %. The concentration of the biological function regulating agent in the fat decomposition promoting agent means the concentration of a collagen peptide in the biological function regulating agent because the content of the first compound is very small. Thus, the concentration of the biological function regulating agent in the fat decomposition promoting agent can be determined by a method identical to the above-described method for measuring the concentration of the biological function regulating agent in the epidermal metabolism promoting agent.

Dosage and Administration, Etc.

Here, the above-described epidermal metabolism promoting agent, fat accumulation inhibiting agent, fat decomposition promoting agent and adiponectin production promoting agent can be orally or parenterally administered in various forms as supplements, medicaments, quasi-pharmaceutical products or the like. When oral administration is performed, the form can be a dosage form such as a tablet, a granule, a capsule, a powder, a solution, a suspension preparation, an emulsion preparation or a paste preparation. It is also possible to mix the above-described dosage form with a functional food described later.

When parenterally administered, the epidermal metabolism promoting agent, the fat accumulation inhibiting agent, the fat decomposition promoting agent and the adiponectin production promoting agent can be provided in dosage forms such as infusion preparations into the body, injection preparations, transdermal preparations (plasters, patches and aerosols), suppositories, nasal drops and inhalants. Examples of preferred dosage forms of the epidermal metabolism promoting agent, the fat accumulation inhibiting agent, the fat decomposition promoting agent and the adiponectin production promoting agent include tablets, granules, capsules, powders, solutions and transdermal preparations.

The dosages of the epidermal metabolism promoting agent, the fat accumulation inhibiting agent, the fat decomposition promoting agent and the adiponectin production promoting agent vary depending on the age, the sex, the body weight and the differential sensitivity of a subject, the administration method, the administration interval, the type of preparation and the like. When the epidermal metabolism promoting agent, the fat accumulation inhibiting agent, the fat decomposition promoting agent and the adiponectin production promoting agent are orally administered, for example, the relevant dosage of each of the agents is preferably 0.0001 to 2500 mg/kg, more preferably 0.0001 to 500 mg/kg a day for an adult. When the dosage form of the epidermal metabolism promoting agent, the fat accumulation inhibiting agent, the fat decomposition promoting agent and the adiponectin production promoting agent is, for example, a tablet, the tablet may comprise the epidermal metabolism promoting agent, the fat accumulation inhibiting agent, the fat decomposition promoting agent or the adiponectin production promoting agent at 0.001 to 80 mass % per tablet, and when the dosage form of the epidermal metabolism promoting agent, the fat accumulation inhibiting agent, the fat decomposition promoting agent and the adiponectin production promoting agent is, for example, a powder, the powder may comprise the epidermal metabolism promoting agent, the fat accumulation inhibiting agent, the fat decomposition promoting agent or the adiponectin production promoting agent at 0.001 to 100 mass %. When parenteral administration is performed, the dosage of each of the epidermal metabolism promoting agent, the fat accumulation inhibiting agent, the fat decomposition promoting agent and the adiponectin production promoting agent can be appropriately determined by referring to a dosage where oral administration is performed. The epidermal metabolism promoting agent, the fat accumulation inhibiting agent, the fat decomposition promoting agent and the adiponectin production promoting agent can be administered once or in several doses a day, or administered once a day or every several days.

The epidermal metabolism promoting agent, the fat accumulation inhibiting agent, the fat decomposition promoting agent and the adiponectin production promoting agent may comprise other active ingredients, carriers for preparations and the like as long as they do not adversely affect the effect of the present invention. Examples of other active ingredients include phosphoric acid (±)-α-tocopherol disodium salts, heparin analogs, allantoin, glycyrrhizic acid, glycyrrhetin, D-amino acids, aminosilane compounds, tiliroside, yuzu extracts, α-glucosyl hesperidin, mulberry leaf extracts, mangosteen fruit skin extracts, α-mangosteen, γ-mangosteen, cacao seed extracts, cacao hull extracts, *ginseng* extracts, lychee polyphenol, leguminous Psophocarpus extracts, *Peucedanum japonicum* extracts, lactic acid bacteria, glabridin, *Euphrasia officinalis* extracts, dried *Pueraria lobata* flower extracts, water shield extracts, Verpa bohemia extracts, crocetin extracts, N-acetylglucosamine, anserine and raspberry ketone. Examples of the pharmaceutically acceptable carrier used in formation of a pharmaceutical preparation include diluents, binders (syrup, gum arabic, gelatin, sorbitol, tragacanth and polyvinylpyrrolidone), excipients (lactose, sucrose, cornstarch, potassium phosphate, sorbitol and glycine), lubricants (magnesium stearate, talc, polyethylene glycol and silica), disintegrants (potato starch) and wetting agents (sodium lauryl sulfate).

Functional Food

The functional food according to the present embodiment comprises the biological function regulating agent. As the functional food, for example, foods for specified health uses and foods with functional claims can be exemplified. The functional food can exhibit the action of the biological function regulating agent, i.e. at least one action selected from the group consisting of an epidermal metabolism promoting action, a fat accumulation inhibiting action, a fat decomposition promoting action and an action of regulating the amount of adipocytokine in a biological body, as, for example, a food for specified health uses or a food with functional claims. In the functional food, the concentration of the biological function regulating agent in, for example, the food for specified health uses or the food with functional claims can be 0.01 to 100 mass %. The concentration of the biological function regulating agent in the functional food means the concentration of a collagen peptide in the biological function regulating agent because the content of the first compound is very small. Thus, the concentration of the biological function regulating agent in the functional food can be determined by a method identical to the above-described method for measuring the concentration of the biological function regulating agent in the epidermal metabolism promoting agent.

Cosmetic Product

The cosmetic product according to the present embodiment comprises the biological function regulating agent. The cosmetic product can be provided as a cosmetic product having a whitening effect, a moisturizing effect, wrinkle preventing and/or wrinkle improving effects and the like under, for example, the epidermal metabolism promoting action of the biological function regulating agent. The concentration of the biological function regulating agent in the cosmetic product may be 0.01 to 100 mass %. The concentration of the biological function regulating agent in the cosmetic product means the concentration of a collagen peptide in the biological function regulating agent because the content of the first compound is very small. Thus, the concentration of the biological function regulating agent in the cosmetic product can be determined by a method identical to the above-described method for measuring the concentration of the biological function regulating agent in the epidermal metabolism promoting agent.

Method for Producing Biological Function Regulating Agent

The method for producing a biological function regulating agent according to the present embodiment is a method for producing a biological function regulating agent comprising a fermented collagen peptide. The method for producing a biological function regulating agent comprises providing koji containing koji mold, and a collagen raw material (first step), and fermenting the collagen raw material with the koji to obtain a biological function regulating agent comprising the fermented collagen peptide (second step).

In the method for producing a biological function regulating agent, the bacterial type of the koji mold is a bacterial type belonging to *Aspergillus*. The collagen raw material is at least any of at least one selected from the group consisting of the following first to sixth groups, collagen extracted from at least one selected from the group, gelatin obtained by treating the collagen, and a gelatin degradation product obtained by hydrolyzing the gelatin:

First group: group consisting of hide, skin, bone, cartilage and tendon of cattle;
Second group: group consisting of hide, skin, bone, cartilage and tendon of pig;
Third group: group consisting of hide, skin, bone, cartilage and tendon of sheep;
Fourth group: group consisting of hide, skin, bone, cartilage and tendon of chicken;
Fifth group: group consisting of hide, skin, bone, cartilage and tendon of ostrich;
Sixth group: group consisting of bone, skin and scale of fish.

The method for producing a biological function regulating agent, which has such a characteristic, enables production of a biological function regulating agent comprising a fermented collagen peptide having at least one action selected from the group consisting of an epidermal metabolism promoting action, a fat accumulation inhibiting action, a fat decomposition promoting action and an action of regulating the amount of adipocytokine in a biological body.

The reason why the biological function regulating agent produced by the above-described production method can have at least one action selected from the group consisting of an epidermal metabolism promoting action, a fat accumulation inhibiting action, a fat decomposition promoting action and an action of regulating the amount of adipocytokine in a biological body is not fully known, but may be explained by the following mechanism. That is, the production method comprises fermenting a collagen raw material with koji to obtain a biological function regulating agent comprising a fermented collagen peptide (second step). The koji is known to comprise a variety of enzymes produced by proliferation of koji mold. Thus, in the second step, such a variety of enzymes may exert their action to decompose or oxidize and reduce polypeptides in the collagen raw material and saccharides in the koji.

Thus, in the second step, it is considered that when the variety of enzymes exert their action to produce a fermented collagen peptide, the fermented collagen peptide includes a collagen peptide containing a dipeptide, a tripeptide, an oligopeptide or a polypeptide having at least any physiological activity selected from the epidermal metabolism promoting action, the fat accumulation inhibiting action, the fat decomposition promoting action and the action of regulating the amount of adipocytokine in a biological body. It is also considered that when the variety of enzymes exert their action to produce a fermented collagen peptide, the fermented collagen peptide includes a compound (non-peptide) having at least any physiological activity selected from the above-described actions. Therefore, it is considered that by the above-described production method, a biological function regulating agent comprising a fermented collagen peptide having at least one action selected from the group consisting of an epidermal metabolism promoting action, a fat accumulation inhibiting action, a fat decomposition promoting action and an action of regulating the amount of adipocytokine in a biological body can be obtained. Hereinafter, the steps in the method for producing a biological function regulating agent according to the present embodiment will be described.

First Step

The first step is a step of providing koji containing koji mold, and a collagen raw material. The first step is carried out for the purpose of providing the materials (koji containing koji mold and a collagen raw material) required for producing the biological function regulating agent.

Collagen Raw Material

The collagen raw material may be at least any of at least one "itself" selected from the group consisting of the following first to sixth groups, "collagen" extracted from at least one selected from the group consisting of the following first to sixth groups, "gelatin" obtained by treating the collagen using a known method such as hot water extraction, and a "gelatin degradation product" obtained by hydrolyzing the gelatin as described above.
First group: group consisting of hide, skin, bone, cartilage and tendon of cattle
Second group: group consisting of hide, skin, bone, cartilage and tendon of pig
Third group: group consisting of hide, skin, bone, cartilage and tendon of sheep
Fourth group: group consisting of hide, skin, bone, cartilage and tendon of chicken
Fifth group: group consisting of hide, skin, bone, cartilage and tendon of ostrich
Sixth group: group consisting of bone, skin and scale of fish.

That is, in the first step, it is preferable that at least one selected from the group consisting of at least one selected from the group consisting of the first to sixth groups, the collagen, the gelatin, and the gelatin degradation product be provided as the collagen raw material. In the first step, one collagen raw material selected from these may be provided, or two or more collagen raw materials may be provided in combination. The group consisting of the first to sixth groups, the collagen, the gelatin and the gelatin degradation product can be all provided by a heretofore known method.

Here, it is preferable that the gelatin be obtained by performing pretreatment by acid treatment or alkali treatment, hot water extraction, purification treatment and sterilization treatment in this order on collagen extracted from at least one selected from the group consisting of the first to sixth groups. This enables provision of gelatin having high safety for the human body etc., and therefore a biological function regulating agent to be produced in the present embodiment can be applied to the applications of the above-described epidermal metabolism promoting agent, fat accumulation inhibiting agent, fat decomposition promoting agent, adiponectin production promoting agent, functional food and cosmetic product. Further, such gelatin is also excellent in economic performance. The pretreatment by acid treatment or alkali treatment, the hot water extraction, the purification treatment and the sterilization treatment can be all performed by a conventionally known method.

The gelatin degradation product can be obtained by subjecting the gelatin to any of hydrolysis with an acid, hydrolysis with a base, hydrolysis with an enzyme and hydrolysis by heating, each of which has been conventionally known. The weight-average molecular weight of the gelatin degradation product should not be particularly limited, and is preferably 20000 or less, more preferably 10000 or less, for example. The lower limit value of the weight-average molecular weight of the gelatin degradation product is 76. The weight-average molecular weight of the gelatin degradation product can be determined by a measurement method identical to that described above for the weight-average molecular weight of a collagen peptide.

Koji Containing Koji Mold

Koji containing koji mold can be provided by a heretofore known method as long as koji that allows the effects of the present embodiment to be obtained by carrying out the second step described later is selected. That is, koji mold as seed koji is inoculated in rice, barley, wheat or a cereal such as soybeans, and then proliferated in the rice, the barley, the wheat or the cereal to obtain the koji. It is preferable that the koji mold be inoculated at 0.01 to 1 mass % with respect to the rice, the barley, the wheat or the cereal. As used herein, the "cereal" includes all of bran, wheat bran, soybean curd lees and defatted soybeans in addition to the above-described soybeans. In provision of koji containing koji mold, it is preferable that a koji chamber for preventing contamination of other bacteria be provided to create an environment which facilitates proliferation of koji mold, and necessary operations be carried out in the koji chamber.

The bacterial type of the koji mold is preferably a bacterial type belonging to *Aspergillus*. The bacterial type of the koji mold is more preferably at least one selected from the group consisting of *Aspergillus sojae, Aspergillus oryzae* and *Aspergillus luchuensis*. Since these bacterial types have been confirmed to be safe for the human body etc., the biological function regulating agent produced in the present embodiment can be easily applied to the applications of the above-described epidermal metabolism promoting agent, fat accumulation inhibiting agent, fat decomposition promoting agent, adiponectin production promoting agent, functional food and cosmetic product. In the first step, koji containing one selected from the group of these bacterial types may be provided, or koji containing two or more selected from the group of the bacterial types may be provided.

Second Step

The second step is a step of fermenting the collagen raw material with the koji to obtain a biological function regulating agent comprising the fermented collagen peptide. The second step is carried out for the purpose of obtaining a fermented collagen peptide contained in the biological function regulating agent. In the second step, for example, the collagen raw material and the koji are put in warm water, and cultured in the warm water for a predetermined time to ferment the collagen raw material with the koji, so that it is possible to obtain a biological function regulating agent comprising the fermented collagen peptide. The value of pH during culture is preferably 2 to 10, more preferably 5 to 8. If the value of pH during culture is lower than 2 or higher than 10, reduction of the molecular weight of the collagen raw material, reduction of the collagen smell and the like may be insufficient.

Specifically, it is preferable that from the collagen raw material at 0.1 to 75 mass %, the koji at 0.1 to 20 mass % in terms of dry mass (dry weight) and water at 5 to 99.8 mass %, a dispersion liquid containing these components at 100 mass % in total be prepared, and the dispersion liquid be adjusted to a pH of 2 to 10, and then cultured for 1 to 24 hours while the dispersion liquid is maintained at a temperature of 10 to 65° C. In this way, a fermented product containing a fermented collagen peptide can be first obtained.

It is also preferable to obtain the fermented product by the following method. That is, first, from the koji at 0.1 to 40 mass % in terms of dry mass (dry weight) and water at 60 to 99.9 mass %, a dispersion liquid containing these components at 100 mass % in total is prepared, and cultured for 1 to 24 hours while the dispersion liquid is maintained at a temperature of 10 to 65° C. The dispersion liquid is coarsely filtered with a nylon mesh, and filtered with diatomaceous earth and cellulose to obtain a koji extraction liquid. Next, from the collagen raw material at 0.1 to 75 mass % and the koji extraction liquid at 0.1 to 99.9 mass %, a dispersion liquid containing these components at 100 mass % in total is prepared, and the dispersion liquid is adjusted to a pH of 2 to 10, and then cultured for 1 to 24 hours while the dispersion liquid is maintained at a temperature of 10 to 65° C. A fermented product containing a fermented collagen peptide can also be obtained by this method. When a fermented product is obtained by applying this method, a biological function regulating agent comprising a fermented collagen peptide can be obtained without carrying out a separation treatment step described later on the fermented product. However, carrying out at least any of a purification step and a deodorization step described later on the fermented product is not excluded.

Here, the temperature of the warm water during culture is preferably 15 to 60° C., more preferably 20 to 50° C. If the temperature of the warm water during culture is below 10° C. or above 65° C., it may be impossible to sufficiently obtain a fermented collagen peptide due to decreased efficiency of fermentation by koji.

Further, the culture time is preferably 2 to 18 hours, more preferably 4 to 8 hours. If the culture time exceeds 24 hours, economic efficiency may be compromised. If the culture time is below 1 hour, fermentation by koji may be insufficient.

The content of the collagen raw material in the warm water during culture is preferably 10 to 45 mass %, more preferably 20 to 40 mass %. If the content of the collagen raw material in the warm water during culture is less than 0.1 mass %, economic efficiency may be compromised. If the content of the collagen raw material in the warm water during culture is above 75 mass %, working efficiency may be compromised.

The content of koji in the dispersion liquid composed of the koji, the collagen raw material and water is preferably 1 to 15 mass %, more preferably 5 to 10 mass %, in terms of dry mass (dry weight). If the content of koji in the warm water during culture is less than 0.1 mass % in terms of dry mass (dry weight), fermentation by koji may be insufficient. If the content of koji in the warm water during culture is above 20 mass % in terms of dry mass (dry weight), economic efficiency may be compromised. The content of koji in the koji extraction liquid is preferably 2 to 25 mass %, more preferably 8 to 16 mass %. If the content of koji is less than 0.1 mass % in terms of dry mass (dry weight) in the koji extraction liquid, fermentation by koji may be insufficient. If the content of koji in the koji extraction liquid is above 40 mass % in terms of dry mass (dry weight), economic efficiency may be compromised.

In the second step, after the fermented product is obtained through the above-described step, the temperature thereof is set to 75° C. or higher depending on the purpose to inactivate the action (activity) of koji mold, so that progression of fermentation of the collagen raw material by koji can be stopped. Specifically, the weight-average molecular weight of the collagen peptide in the fermented product may be measured, and confirmed to be smaller than the molecular average molecular weight of the collagen raw material, or when the culture time reaches a predetermined time, for example 24 hours, the temperature of the fermented product may be set to 75° C. or higher to stop progression of fermentation of the collagen raw material by koji. The weight-average molecular weight of the collagen peptide in the fermented product can be determined by a measurement method identical to that described above for the weight-average molecular weight of a collagen peptide.

Other Steps

It is preferable that the second step include a separation treatment step for separating and obtaining a biological function regulating agent comprising a fermented collagen peptide from the fermented product. For the separation treatment step, conventionally known separation treatment can be applied. A fermented collagen peptide can be separated from the fermented product by separation treatment such as coarse filtration with a nylon mesh, centrifugation or paper filtration with commercially available filter paper. In this way, a biological function regulating agent comprising a fermented collagen peptide comprising a collagen peptide and preferably at least one, more preferably three first compounds selected from the group consisting of isovaleric aldehyde, 1-octen-3-ol, phenylacetaldehyde and methional can be obtained. Since the fermented product comprises a fermented collagen peptide, it is also possible to consider the fermented product itself as a biological function regulating agent.

Further, it is also preferable that the second step include a step of subjecting the biological function regulating agent obtained by applying the separation treatment step or the fermented product to purification treatment for the purpose of enhancing its transparency or the like (purification step). In this purification step, conventionally known purification treatment can be applied, and for example, purification treatment with diatomaceous earth or purification treatment by precision filtration can be performed. Further, deodorization treatment (deodorization step) can also be performed by using activated carbon etc.

The biological function regulating agent obtained as described above can be stored as such in the form of a solution. Further, biological function regulating agent dry powder can be obtained by applying a conventionally known method such as spray drying or drum drying to the biological function regulating agent in the form of a solution, and stored as such. Further, by applying a heretofore known formulation technique to the biological function regulating agent dry powder, any of various dosage forms as described above can be obtained.

Effect

From the above, the method for producing a biological function regulating agent according to the present embodiment enables production of a biological function regulating agent comprising a fermented collagen peptide and having at least one biological function regulating action selected from the group consisting of an epidermal metabolism promoting action, a fat accumulation inhibiting action, a fat decomposition promoting action and an action of regulating the amount of adipocytokine in a biological body on the basis of the fermented collagen peptide.

EXAMPLES

Hereinafter, the present invention will be described in more detail by way of Examples, which should not be construed as limiting the present invention. In the following description, samples 1 to 5 and samples 41 to 49 are biological function regulating agents of Examples, and samples 101 to 104 are collagen peptides or gelatin of Comparative Examples.

Preparation of Sample

Sample 1

First Step

Koji containing koji mold and a collagen raw material were provided in the following procedure.

Provision of Koji Containing Koji Mold

Barley bran koji obtained by inoculating *Aspergillus sojae* (manufactured by Higuchi Matsunosuke Shoten Co., Ltd.) was provided as koji containing koji mold.

Provision of Collagen Raw Material

Pig hide-derived gelatin (trade name: "BCN-HL" manufactured by Nitta Gelatin Inc., weight-average molecular weight: about 65000) was provided as a collagen raw material.

Second Step

A fermented product comprising a fermented collagen peptide was obtained by fermenting the collagen raw material with the koji in the following procedure. First, a dispersion liquid composed of 5 g of the collagen raw material, 1 g (dry weight) of the barley bran koji and 50 mL of RO water was prepared, and cultured for 5 hours while the dispersion liquid was maintained at a temperature of 40° C. Thereafter, the temperature of the dispersion liquid was set to 75° C., and the dispersion liquid was maintained at a temperature of about 75° C. for 10 minutes to inactivate koji mold in the barley bran koji, so that a fermented product comprising a fermented collagen peptide was obtained.

Subsequently, the fermented product was filtered with ADVANTEC FILTER PAPER No. 2 (manufactured by TOYO ROSHI KAISHA Ltd.) to obtain a biological function regulating agent of sample 1.

The biological function regulating agent of sample 1 was an aqueous solution, and the weight-average molecular weight thereof was measured, and confirmed to be smaller than the weight-average molecular weight of the collagen raw material. By analysis using the gas chromatography mass spectrometer, the biological function regulating agent of sample 1 was confirmed to contain isovaleric aldehyde, 1-octen-3-ol, phenylacetaldehyde and methional as the first compound.

Sample 2

In the second step, a dispersion liquid composed of 1 kg of the collagen raw material, 200 g (dry weight) of the barley bran koji and 1500 mL of RO water was prepared, and cultured for 6 hours while the dispersion liquid was maintained at a temperature of 40° C. Thereafter, the temperature of the dispersion liquid was set to 70° C., and the dispersion liquid was maintained at a temperature of about 70° C. for 1 hour to inactivate koji mold in the barley bran koji, so that a fermented product comprising a fermented collagen peptide was obtained. Further, the fermented product was filtered with ADVANTEC FILTER PAPER No. 5 (manufactured by TOYO ROSHI KAISHA Ltd.), and purified by performing filtration with diatomaceous earth. Except for the above, the same procedure as in preparation of sample 1 was carried out to obtain a biological function regulating agent of sample 2.

The biological function regulating agent of sample 2 was in the form of dry powder obtained by using a spray dryer (manufactured by Ookawara Manufacturing Co., Ltd.).

The biological function regulating agent of sample 2 was dry powder, and the weight-average molecular weight thereof was measured, and confirmed to be smaller than the weight-average molecular weight of the collagen raw material. By analysis using the gas chromatography mass spectrometer, the biological function regulating agent of sample 2 was confirmed to contain isovaleric aldehyde, phenylacetaldehyde and methional as the first compound.

Sample 3

First Step

Koji containing koji mold and a collagen raw material were provided in the following procedure.

Provision of Koji Containing Koji Mold

Barley bran koji obtained by inoculating *Aspergillus sojae* (manufactured by Higuchi Matsunosuke Shoten Co., Ltd.) was provided as koji containing koji mold.

Provision of Collagen Raw Material

Pig hide-derived gelatin (trade name: "BCN-HL" manufactured by Nitta Gelatin Inc., weight-average molecular weight: about 65000) was provided as a collagen raw material.

Second Step

A fermented product comprising a fermented collagen peptide was obtained by fermenting the collagen raw material with the koji in the following procedure. First, a dispersion liquid composed of the barley bran koji at 13 mass % (dry weight) and RO water at 87 mass % was prepared, and stirred for 1 hour while the dispersion liquid was maintained at a temperature of 40° C. Thereafter, the dispersion liquid was coarsely filtered with a nylon mesh and filtered with diatomaceous earth and cellulose to obtain a koji extraction liquid. Subsequently, a dispersion liquid composed of the collagen raw material at 40 mass % and the koji extraction liquid at 60 mass % was prepared, and cultured for 6 hours while the dispersion liquid was maintained at a temperature of 40° C. Thereafter, the temperature of the dispersion liquid was set to 80° C., the dispersion liquid was maintained at a temperature of about 80° C. for 60 minutes to perform low-temperature sterilization, and formed into dry powder by using a spray dryer (manufactured by Ookawara Manufacturing Co., Ltd.), so that a biological function regulating agent of sample 3 was obtained.

The biological function regulating agent of sample 3 was dry powder, and the weight-average molecular weight thereof was measured, and confirmed to be smaller than the weight-average molecular weight of the collagen raw material. By analysis using the gas chromatography mass spectrometer, the biological function regulating agent of sample 3 was confirmed to contain isovaleric aldehyde, 1-octen-3-ol, phenylacetaldehyde and methional as the first compound.

Sample 4

A biological function regulating agent of sample 4 was obtained in the same manner as in preparation of sample 3 except that a dispersion liquid composed of the collagen raw material at 40 mass % and the koji extraction liquid at 60 mass % was prepared, and cultured for 6 hours while the dispersion liquid was maintained at a temperature of 40° C., and the temperature of the dispersion liquid was then set to 60° C., and the dispersion liquid was maintained at a temperature of about 60° C. for 60 minutes to perform low-temperature sterilization.

The biological function regulating agent of sample 4 was dry powder, and the weight-average molecular weight thereof was measured, and confirmed to be smaller than the weight-average molecular weight of the collagen raw material. By analysis using the gas chromatography mass spectrometer, the biological function regulating agent of sample 4 was confirmed to contain isovaleric aldehyde, 1-octen-3-ol, phenylacetaldehyde and methional as the first compound.

Sample 5

First Step

Koji containing koji mold and a collagen raw material were provided in the following procedure.

Provision of Koji Containing Koji Mold

Barley bran koji obtained by inoculating *Aspergillus sojae* (manufactured by Higuchi Matsunosuke Shoten Co., Ltd.) was provided as koji containing koji mold.
<Provision of Collagen Raw Material>
Tilapia scale-derived gelatin (manufactured by Nitta Gelatin Inc., weight-average molecular weight: about 150000) was provided as a collagen raw material.

Second Step

A fermented product comprising a fermented collagen peptide was obtained by fermenting the collagen raw material with the koji in the following procedure. First, a dispersion liquid composed of the collagen raw material at 10 mass %, the barley bran koji at 2 mass % (dry weight) and RO water at 88 mass % was prepared, and cultured for 6 hours while the dispersion liquid was maintained at a temperature of 40° C. Thereafter, the temperature of the dispersion liquid was set to 75° C., and the dispersion liquid was maintained at a temperature of about 75° C. for 60 minutes to deactivate koji mold in the barley bran koji, so that a fermented product containing a fermented collagen peptide was obtained.

Subsequently, the fermented product was centrifuged at a centrifugal acceleration of 1610 G for 30 minutes, and the supernatant thereof was taken to obtain a biological function regulating agent of sample 5.

The biological function regulating agent of sample 5 was an aqueous solution, and the weight-average molecular weight thereof was measured, and confirmed to be smaller than the weight-average molecular weight of the collagen raw material. By analysis using the gas chromatography mass spectrometer, the biological function regulating agent of sample 5 was confirmed to contain isovaleric aldehyde, 1-octen-3-ol and phenylacetaldehyde as the first compound.

Sample 101

Dry powder of a collagen peptide (trade name: "Collapep PU" manufactured by Nitta Gelatin Inc., weight-average molecular weight: 630) was provided as sample 101. By analysis using the gas chromatography mass spectrometer, sample 101 was confirmed to be free of the first compound.

Sample 102

Dry powder of pig hide-derived gelatin (trade name: "BCN-HL" manufactured by Nitta Gelatin Inc., weight-average molecular weight: about 65000) was provided as sample 102. Sample 102 was free of a collagen peptide, and was confirmed to be free of the first compound by analysis using the gas chromatography mass spectrometer.

Sample 103

Dry powder of a collagen peptide (trade name: "CP Prototype" manufactured by Nitta Gelatin Inc., weight-average molecular weight: 500 to 1000) was provided as sample 103. By analysis using the gas chromatography mass spectrometer, sample 103 was confirmed to be free of the first compound.

Sample 104

Dry powder of a collagen peptide (trade name: "SCP-5200" manufactured by Nitta Gelatin Inc., weight-average molecular weight: 3000 to 6000) was provided as sample 104. By analysis using the gas chromatography mass spectrometer, sample 104 was confirmed to be free of the first compound.

First Test

By administering the biological function regulating agent of sample 2 to mice, a test was conducted on whether or not the biological function regulating agent had a fat accumulation inhibiting action. Specifically, the first test was conducted in accordance with the following procedure.

Test Method 30 five-week-old male C57BL/6J mice were provided by purchase from CLEA Japan, Inc. The mice were divided into three groups (n=10): a low-fat food intake group (hereinafter, also referred to as a "L group"), a high-fat food intake group (hereinafter, also referred to as a "H group") and a high-fat food and sample 2 (5 mass %) intake group (hereinafter, also referred to as a "FCP group"), and reared for 30 days by giving each group a feed relevant to the group (pair feeding rearing). During rearing, the amount of feed intake and the body weight for each mouse were measured at a predetermined time each day. Table 1 shows the compositions (unit: mass %) of feeds given to the mice of the groups described above. Table 1 also shows the compositions of feeds used in the second test described later.

TABLE 1

| Feed | L group Low-fat food | H group High-fat food | GL group High-fat food + GL | CP group High-fat food + CP | FCP group High-fat food + FCP |
|---|---|---|---|---|---|
| Casein | 20 | 20 | 15 | 15 | 15 |
| Cornstarch | 66.3 | 28.3 | 28.3 | 28.3 | 28.3 |
| Sucrose | — | 13 | 13 | 13 | 13 |
| Oil | 5 | 20 | 20 | 20 | 20 |
| Lard | — | 10 | 10 | 10 | 10 |
| Cellulose | 4 | 4 | 4 | 4 | 4 |
| Choline bitartrate | 0.2 | 0.2 | 0.2 | 0.2 | 0.2 |
| Mineral mix | 3.5 | 3.5 | 3.5 | 3.5 | 3.5 |
| Vitamin mix | 1 | 1 | 1 | 1 | 1 |
| FCP (fermented collagen peptide) | — | — | — | — | 5 |
| CP (collagen peptide) | — | — | — | 5 | — |
| GL (gelatin) | — | — | 5 | — | — |
| Total | 100 | 100 | 100 | 100 | 100 |
| Energy (kcal) | 397.2 | 531.2 | 531.2 | 531.2 | 531.2 |

Next, the mice of the groups were each anesthetized with isoflurane, beheaded to collect blood, and dissected to obtain visceral fat, serum and the liver. As the visceral fat, mesenteric fat, perirenal fat and peritesticular fat were isolated. The amounts of fat (mass (g)) in the respective visceral organs were measured, and then added up to determine the total amount of visceral fat. Further, from the serum, the concentrations of leptin and adiponectin in the serum were quantitatively determined. As a method for quantitative determination, an ELISA method was used, and the leptin concentration was determined in accordance with the protocol of Mouse Leptin Measurement Kit (catalog No: "MS333" manufactured by Morinaga Institute of Biological Science, Inc.). The adiponectin concentration was determined in accordance with the protocol of LBIS Mouse/Rat HMW Adiponectin ELISA Kit (catalog No: "634-13071" manufactured by FUJIFILM Wako Pure Chemical Corporation).

For the liver, the following treatment was performed. First, 0.5 g of the liver was homogenized in 2.5 mL of a 1.15 mass % potassium chloride (KCl) solution, and put in an ice-cooled test tube. Further, the test tube was centrifuged (gravitational acceleration: 9830 G, 10 min, 4° C.), and the supernatant thereof was taken as a coarse enzyme liquid. Subsequently, for the coarse enzyme liquid, the intensity of fatty acid synthetase (FAS) activity was determined by measuring enzyme activity (wavelength: 340 nm) from the rate of decline of NAPDH in the presence of 100 μM malonyl-CoA and 25 μM acetyl CoA in accordance with methods described in Nepokroeff et al., (Methods Enzymol, 35: 37-44, 1975) and Kelley et al., (Biochem. J, 235: 87-90, 1986). Further, for the coarse enzyme liquid, the intensity of fatty acid degrading enzyme (carnitine palmitoyltransferase: CPT) was determined by measuring enzyme activity (wavelength: 412 nm) from the reaction rate of dithionitrobenzoic acid (DTNB) in the presence of 2 mM palmitoyl CoA and 125 mM L-carnitine in accordance with a method described in Markwell et al., (J Biol. Chem, 248: 3426-3432, 1973). FIGS. 1 to 9 show the results. For significant differences between the groups (L group, H group and FCP group) in FIGS. 1 to 9, a Bonferrioni multiple comparison test was conducted, and $P<0.05$ was determined as being statistically significant.

<Discussion>

FIG. 1 is a graph showing changes in body weight of the mice of the groups in the first test. From FIG. 1, it is understood that body weight increase in the FCP group is significantly inhibited as compared to that of the H group.

Figure 2:
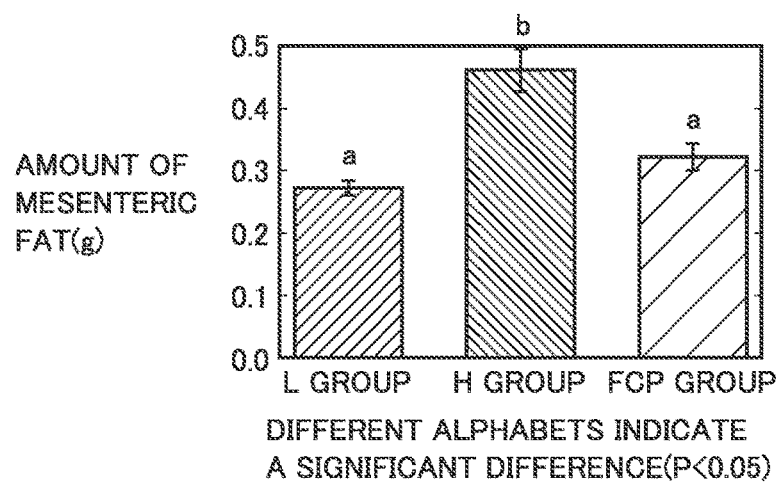
FIG. 2 is a graph showing the amounts of mesenteric fat in the mice of the groups in the first test.
Figure 3:
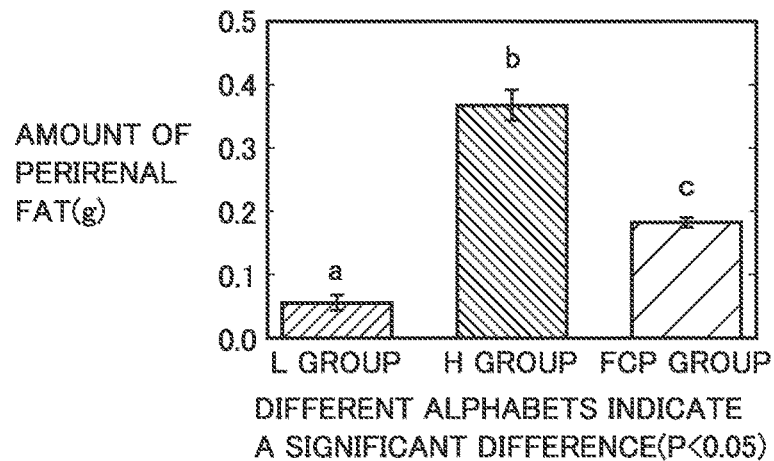
FIG. 3 is a graph showing the amounts of perirenal fat in the mice of the groups in the first test.
Figure 4:
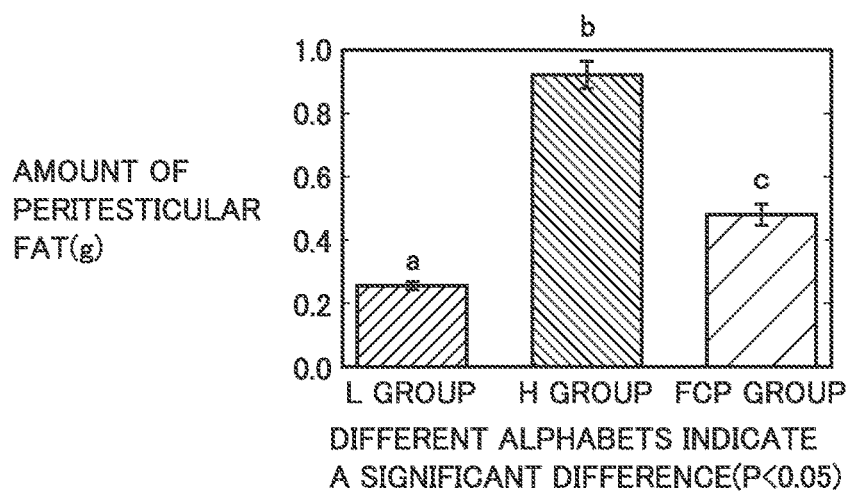
FIG. 4 is a graph showing the amounts of peritesticular fat in the mice of the groups in the first test.
Figure 5:
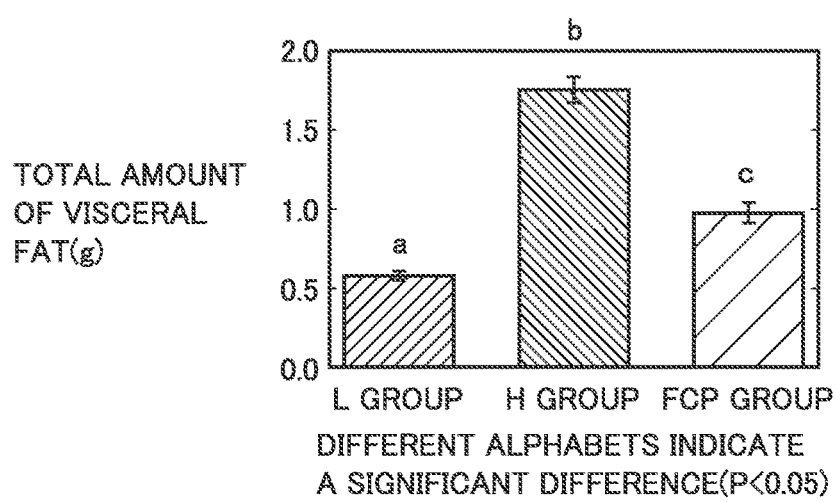
FIG. 5 is a graph showing total amounts of visceral fat in the mice of the groups in the first test.

FIG. 2 is a graph showing the amounts of mesenteric fat in the mice of the groups in the first test. FIG. 3 is a graph showing the amounts of perirenal fat in the mice of the groups in the first test. FIG. 4 is a graph showing the amounts of peritesticular fat in the mice of the groups in the first test. FIG. 5 is a graph showing total amounts of visceral fat in the mice of the groups in the first test. From FIGS. 2 to 5, it is evaluated that fat accumulation in organs in the FCP group is significantly inhibited as compared to that in the H group. Accordingly, it is suggested that in the FCP group, a fat accumulation inhibiting effect is obtained.

Figure 6:
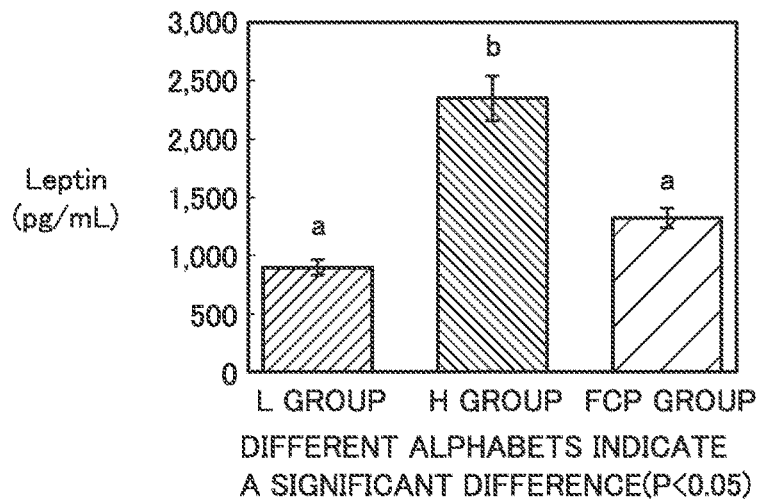
FIG. 6 is a graph showing the concentrations of leptin in the serum of the mice of the groups in the first test.
Figure 7:
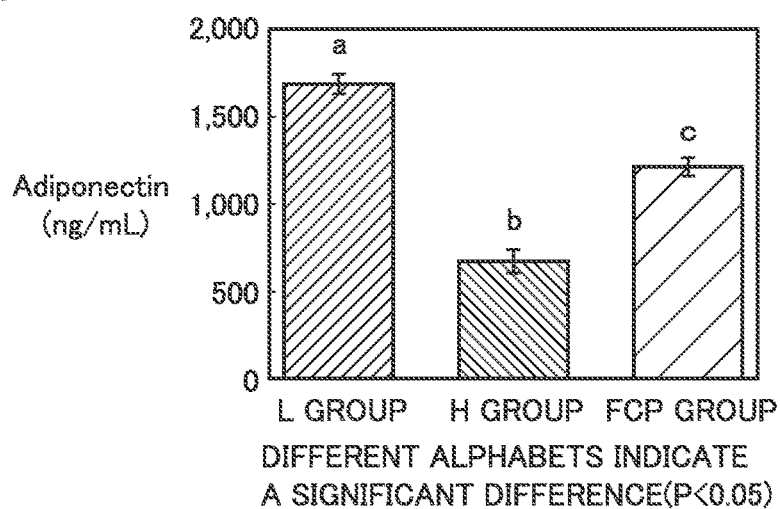
FIG. 7 is a graph showing the concentrations of adiponectin in the serum of the mice of the groups in the first test.

FIG. 6 is a graph showing the concentrations of leptin in the serum of the mice of the groups in the first test. FIG. 7 is a graph showing the concentrations of adiponectin in the serum of the mice of the groups in the first test. From FIGS. 6 and 7, it is evaluated that the blood concentration of leptin in the FCP group is significantly lower as compared to that in the H group, and the blood concentration of adiponectin in the FCP group is significantly higher as compared to that in the H group. Accordingly, it is suggested that in the FCP group, a fat accumulation inhibiting effect is obtained through the action of regulating the amount of adipocytokine in a biological body.

Figure 8:
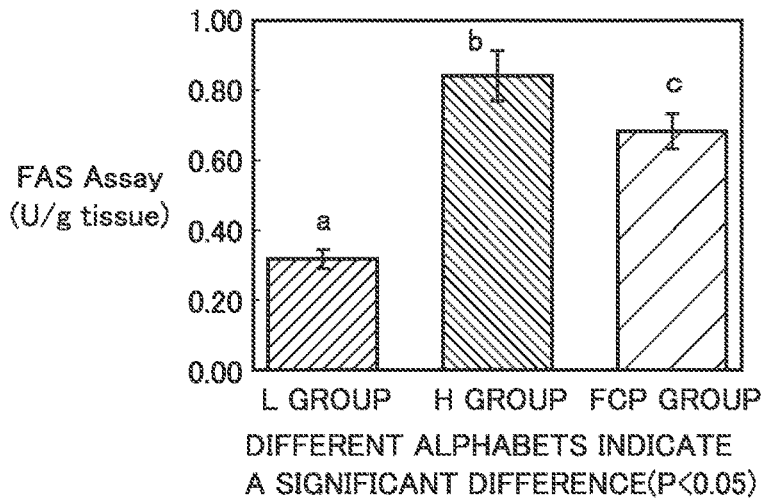
FIG. 8 is a graph showing the intensities of hepatic FAS (fatty acid synthetase) activity in the mice of the groups in the first test.
Figure 9:
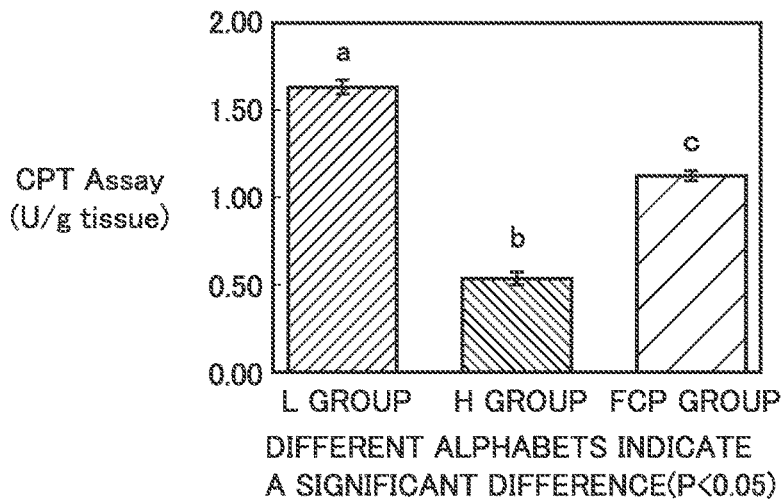
FIG. 9 is a graph showing the intensities of hepatic CPT (carnitine palmitoyltransferase) activity in the mice of the groups in the first test.

FIG. 8 is a graph showing the intensities of hepatic FAS activity in the mice of the groups in the first test. FIG. 9 is a graph showing the intensities of hepatic CPT activity in the mice of the groups in the first test. From FIGS. 8 and 9, it is evaluated that synthesis of fatty acids in the FCP group is significantly inhibited as compared to that in the H group, and decomposition of fatty acids in the FCP group is significantly promoted as compared to that in the H group. Accordingly, it is suggested that in the FCP group, a fat accumulation inhibiting effect is obtained.

[Second Test]

The biological function regulating agent of sample 2 was administered to mice to conduct a test on whether or not the biological function regulating agent had a fat accumulation inhibiting action. Specifically, the second test was conducted in accordance with the following procedure.

Test Method 40 five-week-old male C57BL/6J mice were provided by purchase from CLEA Japan, Inc. The mice were divided into five groups (n=8): a L group, a H group, a FCP group, a high-fat food and sample 101 (5 mass %) intake group (hereinafter, also referred to as a "CP group") and a high-fat food and sample 102 (5 mass %) intake group (hereinafter, also referred to as a "GL group"), and reared for 30 days by giving each group a feed relevant to the group (pair feeding rearing). During rearing, the amount of feed intake and body weight for each mouse were measured at a predetermined time each day. The compositions of feeds given to the mice of the groups are as shown in Table 1 above.

Figure 10:
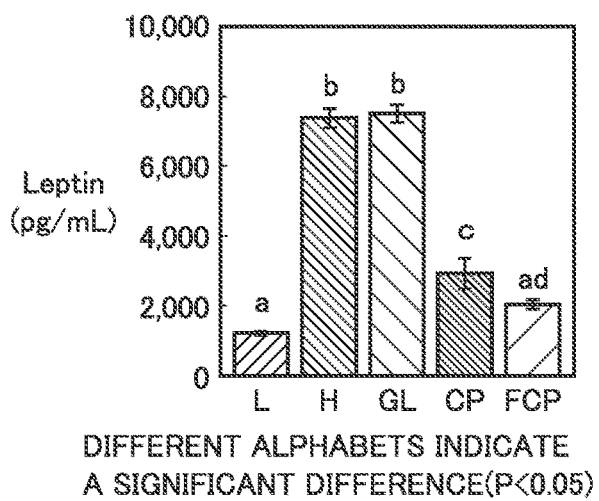
FIG. 10 is a graph showing the concentrations of leptin in the serum of the mice of the groups in the second test.
Figure 11:
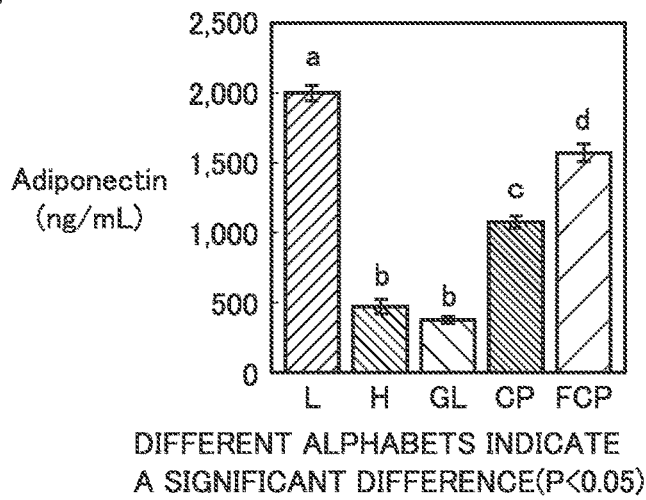
FIG. 11 is a graph showing the concentrations of adiponectin in the serum of the mice of the groups in the second test.

Next, the mice of the groups were each anesthetized with isoflurane, beheaded to collect blood, and dissected to obtain visceral fat and serum. Subsequently, from the visceral fat, the amount of fat in each visceral organ and the total amount of visceral fat were determined in the same manner as in the first test. Further, from the serum, the concentrations of leptin and adiponectin in the serum were quantitatively determined in the same manner as in the first test. Table 2 shows the results of the amount of fat in each organ and the total amount of visceral fat (unit: g). FIGS. 10 and 11 show the results of the concentration of leptin and the concentration of adiponectin in the serum. For significant differences between the groups (L group, H group, GL group, CP group and FCP group) in FIGS. 10 and 11, a Bonferrioni multiple comparison test was conducted, and P<0.05 was determined as being statistically significant.

TABLE 2

|  | L group | H group | GL group | CP group | FCP group |
|---|---|---|---|---|---|
| Amount of mesenteric fat | 0.311 ± 0.024 | 0.500 ± 0.034 | 0.553 ± 0.055 | 0.453 ± 0.029 | 0.339 ± 0.012 |
| Amount of perirenal fat | 0.089 ± 0.003 | 0.388 ± 0.037 | 0.375 ± 0.044 | 0.344 ± 0.025 | 0.225 ± 0.019 |
| Amount of peritesticular fat | 0.398 ± 0.016 | 1.09 ± 0.05 | 1.08 ± 0.12 | 0.945 ± 0.057 | 0.728 ± 0.027 |
| Total amount of visceral fat | 0.798 ± 0.030 | 1.98 ± 0.11 | 2.01 ± 0.21 | 1.74 ± 0.10 | 1.29 ± 0.05 |

Discussion

From Table 2, it is evaluated that fat accumulation in each organ in the FCP group is inhibited as compared to that in the H group. Further, it is evaluated that fat accumulation in each organ in the FCP group is also inhibited as compared to that in the CP group and the GL group. Accordingly, it is indicated that in the FCP group, a fat accumulation inhibiting effect is obtained.

FIG. 10 is a graph showing the concentrations of leptin in the serum of the mice of the groups in a second test. FIG. 11 is a graph showing the concentrations of adiponectin in the serum of the mice of the groups in the second test. From FIGS. 10 and 11, it is evaluated that the blood concentration of leptin in the FCP group is lower as compared to that in the H group, and the blood concentration of adiponectin in the FCP group is higher as compared to that in the H group. Further, it is evaluated that the blood concentration of leptin in the FCP group is lower as compared to that in the CP group and the GL group, and the blood concentration of adiponectin in the FCP group is higher as compared to that in the CP group and the GL group. Accordingly, it is suggested that in the FCP group, a fat accumulation inhibiting effect is obtained under the action of regulating the amount of adipocytokine in a biological body.

Third Test

By adding the biological function regulating agents of samples 1 and 2, and samples 101 and 103 to fat cells differentiated from mouse-derived precursor fat cells (3T3-L1, passage number: 5 passages, 9 PDL), a test was conducted on whether or not the biological function regulating agents of samples 1 and 2 had a fat accumulation inhibiting action. Specifically, the third test was conducted in accordance with the following procedure.

Test Method

The mouse-derived precursor fat cells (manufactured by Research Resources Bank, Resource No. JCRB 9014, Lot No. 01282009) were precultured in a culture medium (DMEM/F12 medium (passage culture, catalog No: "11330-032", manufactured by Gibco Company, containing 10 mass % FBS, penicillin and streptomycin). Subsequently, from the medium and the cells subjected to the preculture, a cell suspension liquid containing the cells at $3 \times 10^4$ cells/mL was prepared. Further, 5 mL of the cell suspension liquid was seeded in each of 60 mm dishes (catalog No: Corning, Cat. No. 430166) ($1.5 \times 10^5$ cells/dish), and cultured for 2 days under the condition of 37° C. (5 vol % $CO_2$). The medium in each dish was replaced by a differentiation-inducing medium in which isobutylmethylxanthine (IBMX) and dexamethasone attached to Adipogenesis Assay Kit (catalog No: "ECM 950", manufactured by Millipore Corporation) were added to final concentrations of 0.5 mM and 1 µM, respectively, and culture was further performed for 2 days under the condition of 37° C. (5 vol % $CO_2$). Thereafter, the differentiation-inducing medium was replaced by a differentiation medium to which insulin attached to Adipogenesis Assay Kit (catalog No: "ECM 950", manufactured by Millipore Corporation) were added to final concentrations of 10 µg/mL, and culture was further performed for 2 days under the condition of 37° C. (5 vol % $CO_2$). It was confirmed that the cells in each dish were differentiated into fat cells, followed by replacement of the differentiation medium by the passage medium. To the fat cells in the passage medium, the biological function regulating agents of samples 1 and 2, and samples 101 and 103 were added to a final concentration of 0.1 mass %, and a berberine chloride solution (catalog No: "027-11781", manufactured by FUJIFILM Wako Pure Chemical Corporation) to a final concentration of 2 µg/mL, and to the residual fat cells in the passage medium, RO water was added. Culture was performed for 2 days under the condition of 37° C. (5 vol % $CO_2$). Samples 1, 2, 101 and 103, the berberine chloride solution and the RO water were each added to three dishes. Thereafter, the passage medium was replaced by a new passage medium, samples 1, 2, 101 and 103 were added again to a final concentration of 0.1 mass %, the berberine chloride solution was added again to a final concentration of 2 µg/mL, and RO water was added again to each relevant dish.

Next, in accordance with the protocol of the adipogenesis assay kit, an Oil Red O solution attached to the kit was added to each dish at normal temperature. That is, fat cells in each of the culture media containing samples 1, 2, 101 and 103, the berberine chloride solution and the RO water were washed twice with PBS (phosphate buffered saline), and 1.25 mL of the Oil Red O solution at a concentration of 36 mass % was then added to each dish. Thereafter, the cells were washed twice with 2.5 mL of isopropanol at a concentration of 60 mass %, and 625 µL of isopropanol at a concentration of 99 mass % was added to obtain an extraction liquid containing fat cells and Oil Red O from each dish. 200 µL of the extraction liquid was transferred to a 96-well plate, and the absorbance at OD 520 nm was measured with an absorption spectrometer (trade name: "Synergy HTX" manufactured by Biotech Japan Corporation). It is evaluated that the higher the value of the absorbance at OD 520 nm, the more likely the fat accumulation is to occur in fat cells. Here, the extraction liquid obtained from dishes containing RO water is a blank. The extraction liquid obtained from dishes containing the berberine chloride solution is a positive control.

The fat accumulation ratio in fat cells containing each sample, the berberine chloride solution or RO water was determined in accordance with the following calculation expression.

Fat accumulation ratio (%)=[(measured value at OD 520 nm for each sample)/(measured value at OD 520 nm for blank)×100]

Table 3 shows the results. In Table 3, the average value (Ave) and the standard deviation of the fat accumulation ratios of three test specimens in each sample are shown. Further, with regard to Table 3, statistical processing was performed on each measured value to determine a significant difference in whether or not fat accumulation was inhibited. For the statistical processing, analytical processing software (trade name: "STAT Mate V" manufactured by ATOMS) was used. The significant difference was determined by performing one-way analysis of variance (one-way ANOVA) with a confidence interval having a confidence coefficient of 95% and a Turkey test as a post hoc test. In Table 3, $p<0.001$ is represented by *, $p<0.01$ is represented by , and $p<0.05$ is represented by *.

TABLE 3

| Sample | Final conc. | Blank = 100 | | VS Blank | |
|---|---|---|---|---|---|
| | | Ave | Standard deviation | Tukey test | Assessment |
| Blank | — | 100 | 10.93 | — | — |
| Berberine chloride | 2 µg/mL | 37 | 0.80 | 0.001 | *** |
| Sample 1 | 0.1 mass % | 36 | 3.20 | 0.001 | *** |
| Sample 2 | 0.1 mass % | 72 | 3.34 | 0.05 | * |
| Sample 101 | 0.1 mass % | 125 | 2.73 | — | — |
| Sample 103 | 0.1 mass % | 133 | 11.38 | — | — |

Discussion

From Table 3, it is evaluated that the biological function regulating agents of samples 1 and 2 inhibit fat accumulation in fat cells as compared to samples 101 and 103.

Fourth Test

By adding biological function regulating agents of samples 41 to 49 described later to fat cells differentiated from mouse-derived precursor fat cells (3T3-L1, passage number: 7 passages, 13 PDL), a test was conducted on whether or not the biological function regulating agents of samples 41 to 49 had a fat accumulation inhibiting action. Specifically, the fourth test was conducted in accordance with the following procedure.

Test Method

Preparation of Samples 41 to 49

The biological function regulating agents of samples 41 to 49 were prepared in the same manner as in preparation of the biological function regulating agent of sample 2 except that conditions for fermenting a collagen raw material with the koji in the second step were as shown in Table 4. For sample 43, the conditions for fermenting the collagen raw material with the koji were the same as those for sample 2. Table 4 also shows the weight-average molecular weights of collagen peptides contained in the samples.

TABLE 4

| Sample | Reaction temperature (° C.) | Reaction time (h) | Reaction pH | Weight-average molecular weight (Mw) |
|---|---|---|---|---|
| Sample 41 | 40 | 2 | 5.57 | 2995 |
| Sample 42 | 40 | 4 | 5.57 | 1949 |
| Sample 43 | 40 | 6 | 5.57 | 1747 |
| Sample 44 | 60 | 2 | 5.75 | 2536 |
| Sample 45 | 60 | 4 | 5.75 | 2286 |
| Sample 46 | 60 | 6 | 5.75 | 2182 |
| Sample 47 | 40 | 2 | 6.47 | 2727 |
| Sample 48 | 40 | 4 | 6.47 | 1762 |
| Sample 49 | 40 | 6 | 6.47 | 1578 |

Test Method

The fourth test was conducted in the same manner as in the third test except that the passage number for mouse-derived precursor fat cells (3T3-L1) was "7 passages, 13 PDL", and the final concentration of each of samples 41 to 49 added to fat cells in the dish was 0.2 mass %. Table 5 shows the results.

TABLE 5

| | | Blank = 100 | |
|---|---|---|---|
| | Final conc. | Ave | Standard deviation |
| Blank | — | 100 | 6 |
| Sample 41 | 0.2 mass % | 83 | 4 |
| Sample 42 | 0.2 mass % | 80 | 1 |
| Sample 43 | 0.2 mass % | 84 | 5 |
| Sample 44 | 0.2 mass % | 86 | 3 |
| Sample 45 | 0.2 mass % | 87 | 2 |
| Sample 46 | 0.2 mass % | 82 | 2 |
| Sample 47 | 0.2 mass % | 86 | 6 |
| Sample 48 | 0.2 mass % | 87 | 4 |
| Sample 49 | 0.2 mass % | 89 | 6 |

Discussion

From Table 5, it is evaluated that the biological function regulating agents of samples 41 to 49 all inhibit fat accumulation in fat cells as compared to the blank. In the fourth test, the presence or absence of a significant difference in inhibition of fat accumulation was not determined.

Fifth Test

By adding the biological function regulating agents of samples 1 and 2, and sample 104 to human normal epidermal keratinocytes NHEK (NB) (catalog No: "KK 4009", Lot. 05298, manufactured by KURABO INDUSTRIES LTD.), a test was conducted on whether or not the biological function regulating agents of samples 1 and 2 had an epidermal metabolism promoting action. Specifically, the fifth test was conducted in accordance with the following procedure.

Test Method

Human normal epidermal keratinocytes NHEK (NB) (manufactured by KURABO INDUSTRIES LTD.) were precultured in a culture medium (trade name: "HuMedia KG2" manufactured by KURABO INDUSTRIES LTD.). Subsequently, from the medium and the cells subjected to the preculture, a cell suspension liquid containing the cells at $1.5 \times 10^4$ cells/mL was prepared, and the cell suspension liquid was seeded in each well of a six-well plate (catalog No: "353046", manufactured by Falcon Company) at $3 \times 10^4$ cells, and cultured for 4 days. Next, the cells were confirmed to be 90 area %-subconfluent in the plate, and the medium in the wells of respective plates was then replaced by a test medium (trade name: "HuMedia KB2" manufactured by KURABO INDUSTRIES LTD.). Further, biological function regulating agents of samples 1 and 2, sample 104 and RO water were added to the wells of respective plates to a final concentration of 0.1 mass %, and cultured under the condition of 37° C. (5 vol % $CO_2$). Here, cells in the plates for measuring a keratin 10 (KRT 10) gene expression level described later were cultured for 24 hours, and cells in the plates for measuring involucrin (Ivl) and transglutaminase (TGM 1) gene expression levels described later were cultured for 48 hours.

Thereafter, the wells were washed twice with PBS, and 1 mL of TRIzol reagent (catalog No: "15506-026", manufactured by Thermo Fisher Scientific) was added to each well. One minute thereafter, a scraper was used to all cells in each well were collected in a 1.5 mL centrifuging tube. Subsequently, total RNA was extracted from the cells in accordance with the TRIzol protocol, and the absorbance at 260 nm was then measured to adjust the concentration of total RNA to 1 μg/mL. Total RNA, whose purity was 1.8 or more when calculated by A260/A280, was used. cDNA was obtained by performing reverse transcription of the total RNA using High Capacity RNA to cDNA Kit (catalog No: "4387406", manufactured by Life Technologies Corporation), and subjected to real-time RT-PCR.

In the real-time RT-PCR, the mRNA levels of KRT 10 (primer: Hs1043114_gl manufactured by thermo Fisher Scientific), TGM 1 (primer: Hs01070310_ml, manufactured by thermo Fisher Scientific) and Ivl (primer: Hs00846307_sl, manufactured by thermo Fisher Scientific) as target genes were measured for each sample. As an internal standard (corrected gene), GAPDH (catalog No: "4352934E", manufactured by thermo Fisher Scientific) was used. For calculation, a calibration curve method was used. As primers and probes, FAM dyes were used. The real-time PCR was performed by an apparatus (trade name: "Step One Plus" manufactured by Applied Biosystems), and a reagent kit (trade name: "TaqMan (registered trademark) fast advanced master mix", catalog No: "4444556", manufactured by Applied Biosystems) was used. PCR conditions were such that denaturization (95° C., 20 sec, 1 cycle) and 40 cycles of annealing (95° C., 1 sec) and polymerization (60° C., 20 sec) were performed. Here, total RNA (cDNA) obtained from the well containing RO water is a blank. Tables 6 to 8 show the results.

Table 6 shows relative values of gene expression levels of KRT 10 in samples 1, 2 and 104 against the blank (average value (Ave) for three test specimens and standard deviation in each sample). Table 7 shows relative values of gene expression levels of TGM 1 in samples 2 and 104 against the blank (average value (Ave) for three test specimens and standard deviation in each sample). Table 8 shows relative values of gene expression levels of Ivl in samples 1, 2 and 104 against the blank (average value (Ave) for three test specimens and standard deviation in each sample). Further, Tables 6 to 8 show significant differences in whether or not expression of each gene was increased as determined by performing statistical processing on each measured value. For the statistical processing, analytical processing software (trade name: "Excel" manufactured by Microsoft Corporation) was used. The significant difference was determined by conducting a paired-T-test. $p<0.001$ is represented by *, $p<0.01$ is represented by , and $p<0.05$ is represented by *.

TABLE 6

| | | | KRT10 | | |
| --- | --- | --- | --- | --- | --- |
| | | | Blank = 100 | | |
| | | | | VS Blank | |
| | | | Standard | | |
| Sample | Final conc. | Ave | deviation | Test | Assessment |
| Blank | — | 100 | 2.24 | — | — |
| Sample 1 | 0.1 mass % | 126 | 4.03 | 0.0013 | ** |
| Sample 2 | 0.1 mass % | 256 | 7.2 | 0.000008 | *** |
| Sample 104 | 0.1 mass % | 98 | 17.31 | 0.93 | — |

TABLE 7

| | | | TGM1 | | |
| --- | --- | --- | --- | --- | --- |
| | | | Blank = 100 | | |
| | | | | VS Blank | |
| | | | Standard | | |
| Sample | Final conc. | Ave | deviation | Test | Assessment |
| Blank | — | 100 | 32.47 | — | — |
| Sample 2 | 0.1 mass % | 311 | 23.88 | 0.0018 | *** |
| Sample 104 | 0.1 mass % | 122 | 17.31 | 0.15 | — |

TABLE 8

| | | | Ivl | | |
| --- | --- | --- | --- | --- | --- |
| | | | Blank = 100 | | |
| | | | | VS Blank | |
| | | | Standard | | |
| Sample | Final conc. | Ave | deviation | Test | Assessment |
| Blank | — | 100 | 23.37 | — | — |
| Sample 1 | 0.1 mass % | 250 | 24 | 0.0032 | ** |
| Sample 2 | 0.1 mass % | 526 | 60.12 | 0.0007 | *** |
| Sample 104 | 0.1 mass % | 109 | 2.07 | 0.65 | — |

Discussion

Tables 6 to 8 reveal that the biological function regulating agents of samples 1 and 2 can increase the expression levels of KRT 10, TGM 1 and Ivl genes in human epidermal cells. Accordingly, it is indicated that epidermal metabolism is promoted by the increased expression of the genes.

Sixth Test

By conducting the fifth test using the biological function regulating agents of samples 41 to 49, a test was conducted on whether or not the biological function regulating agents of samples 41 to 49 had an epidermal metabolism promoting action. Tables 9 to 11 show the results.

Table 9 shows relative values of gene expression levels of KRT 10 in samples 41 to 49 against the blank (average value (Ave) for three test specimens and standard deviation in each sample). Table 10 shows relative values of gene expression levels of TGM 1 in samples 41 to 49 against the blank (average value (Ave) for three test specimens and standard deviation in each sample). Table 11 shows relative values of gene expression levels of Ivl in samples 41 to 49 against the blank (average value (Ave) for three test specimens and standard deviation in each sample). In the sixth test, the presence or absence of a significant difference in epidermal metabolism promoting action (increased expression of the genes) was not determined.

TABLE 9

| | KRT10 | | |
| --- | --- | --- | --- |
| | | Blank = 100 | |
| Sample | Final conc. | Ave | Standard deviation |
| Blank | — | 100 | 27.5 |
| Sample 41 | 0.1 mass % | 198 | 15.01 |
| Sample 42 | 0.1 mass % | 141 | 4.15 |
| Sample 43 | 0.1 mass % | 129 | 5.72 |
| Sample 44 | 0.1 mass % | 206 | 21.47 |
| Sample 45 | 0.1 mass % | 181 | 15.27 |
| Sample 46 | 0.1 mass % | 189 | 18.79 |
| Sample 47 | 0.1 mass % | 152 | 6.6 |
| Sample 48 | 0.1 mass % | 172 | 27.69 |
| Sample 49 | 0.1 mass % | 163 | 13.67 |

TABLE 10

| | TGM1 | | |
| --- | --- | --- | --- |
| | | Blank = 100 | |
| Sample | Final conc. | Ave | Standard deviation |
| Blank | — | 100 | 13.84 |
| Sample 41 | 0.1 mass % | 161 | 17.18 |
| Sample 42 | 0.1 mass % | 178 | 31.35 |
| Sample 43 | 0.1 mass % | 164 | 15.4 |
| Sample 44 | 0.1 mass % | 185 | 23.35 |
| Sample 45 | 0.1 mass % | 159 | 25.24 |
| Sample 46 | 0.1 mass % | 169 | 8.32 |
| Sample 47 | 0.1 mass % | 170 | 12.81 |
| Sample 48 | 0.1 mass % | 190 | 16.72 |
| Sample 49 | 0.1 mass % | 177 | 18.6 |

TABLE 11

| | Ivl | | |
| --- | --- | --- | --- |
| | | Blank = 100 | |
| Sample | Final conc. | Ave | Standard deviation |
| Blank | — | 100 | 26.98 |
| Sample 41 | 0.1 mass % | 237 | 13.24 |
| Sample 42 | 0.1 mass % | 259 | 26.68 |
| Sample 43 | 0.1 mass % | 214 | 1.27 |
| Sample 44 | 0.1 mass % | 254 | 6.97 |
| Sample 45 | 0.1 mass % | 254 | 11.98 |
| Sample 46 | 0.1 mass % | 255 | 17.67 |
| Sample 47 | 0.1 mass % | 236 | 11.15 |
| Sample 48 | 0.1 mass % | 261 | 18.88 |
| Sample 49 | 0.1 mass % | 264 | 8.61 |

Discussion

Tables 9 to 11 reveal that the biological function regulating agents of samples 41 to 49 can increase the expression levels of KRT 10, TGM 1 and Ivl genes in human epidermal cells. Accordingly, it is indicated that epidermal metabolism is promoted by the increased expression of the genes.

Seventh Test

In the same way as in the first test, the biological function regulating agent of sample 2 was administered to a mouse, and using a change in body weight of the mouse as an indicator, a test was conducted on whether or not the biological function regulating agent had a fat accumulation inhibiting action. It is to be noted that for the FCP group, the concentration of sample 2 given was half that in the first test (2.5 mass % feed).

Discussion

Figure 12:
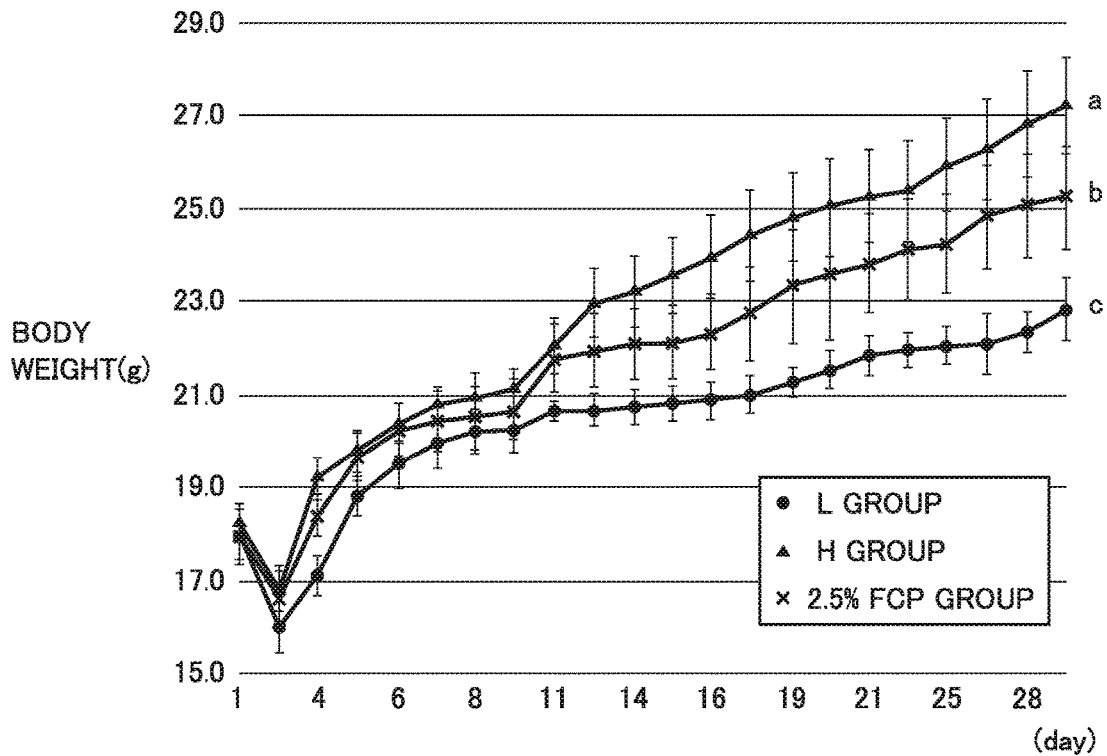
FIG. 12 is a graph showing changes in body weight of the mice of the groups in the seventh test.

FIG. 12 is a graph showing changes in body weight of the mice of the groups in a seventh test. From FIG. 12, it is understood that body weight increase in the FCP group is significantly inhibited as compared to that in the H group.

[Eighth Test]

By administering the biological function regulating agents of samples 3 and 4 to mice made overweight by loading glucose, a test was conducted on whether or not the biological function regulating agents had a fat accumulation inhibiting action. Specifically, the eighth test was conducted in accordance with the following procedure.

<Test Method>

48 five-week-old male C57BL/6J mice were provided by purchase from CLEA Japan, Inc. By giving the mice normal food (AIN-93G purified feed) and water containing fructose (manufactured by FUJIFILM Wako Pure Chemical Corporation) at 15 mass % (hereinafter, also referred to as "15 mass % fructose water") for 42 days, the body weights of the mice were intentionally increased. Next, the 48 mice having an increased body weight were divided into six groups (n=8): a normal group (A group) to be given the normal food and water, a negative control group (B group) to be given the normal food and 15 mass % fructose water, a FCP-3 group (C group) to be given a diet obtained by replacing 6 mass % of casein contained in the normal food at 20 mass % by the biological function regulating agent of sample 3 and 15 mass % fructose water, a FCP-4 group (D group) to be given a diet obtained by replacing 6 mass % of casein contained in the normal food at 20 mass % by the biological function regulating agent of sample 4 and 15 mass % fructose water, a Collapep PU group (E group) given a diet obtained by replacing 6 mass % of casein contained in the normal food at 20 mass % by sample 101 and 15 mass % fructose water, and a SCP-5200 group (F group) to be given a diet obtained by replacing 6 mass % of casein contained in the normal food at 20 mass % by sample 104 and 15 mass % fructose water, provided that there was no difference in body weight between the groups.

Thereafter, a relevant diet and water were given to the mice of each groups for 35 days to rear the mice (pair feeding rearing). During rearing, the amount of feed intake and body weight in each mouse were measured at a predetermined time each day. Table 12 shows a listing of diets (unit: mass %) and water given to the mice of the groups. In the section "water/15 mass % fructose water" in Table 12, "W" means that water was given, and "F" means that fructose water was given. Here, the normal food (AIN-93G purified feed) has a composition of casein at 20 mass %, corn starch at 26.75 mass %, sucrose at 10 mass %, corn oil at 20 mass %, α-corn starch at 13.2 mass %, cellulose at 5 mass %, colin bitartrate at 0.25 mass %, mineral mix (AIN-93) at 3.5 mass %, vitamin mix (AIN-93G) at 1 mass % and L-cystine at 0.3 mass %.

TABLE 12

| Component | A group AIN-93G purified feed | B group AIN-93G purified feed | C group AIN-93G purified feed + Sample 3 | D group AIN-93G purified feed + Sample 4 | E group AIN-93G purified feed + Sample 101 | F group AIN-93G purified feed + Sample 104 |
|---|---|---|---|---|---|---|
| AIN-93G purified feed | 100 | 100 | 94 | 94 | 94 | 94 |
| Sample 3 | — | — | 6 | — | — | — |
| Sample 4 | — | — | — | 6 | — | — |
| Sample 101 | — | — | — | — | 6 | — |
| Sample 104 | — | — | — | — | — | 6 |
| Total | 100 | 100 | 100 | 100 | 100 | 100 |
| water/15 mass % fructose water | W | F | F | F | F | F |

Next, the mice of the groups were each anesthetized with isoflurane, beheaded to collect blood, and dissected to obtain visceral fat, serum and the liver. As the visceral fat, mesenteric fat, perirenal fat and peritesticular fat were isolated. The amounts of fat (mass (g)) in the respective visceral organs were measured, and then added up to determine the total amount of visceral fat. Further, from the serum, the blood glucose level, the amount of insulin and the concentration of leptin in the serum were quantitatively determined. For measurement of the blood glucose level, Glutest Sensor (manufactured by Sanwa Kagaku Kenkyusho Co., Ltd.) was used. For measurement of the amount of insulin, LBIS insulin-Mouse T (manufactured by FUJIFILM Wako Pure Chemical Corporation) was used. The concentration of leptin was determined in accordance with the protocol of Morinaga Mouse/Rat Leptin Measurement Kit (manufactured by Morinaga Institute of Biological Science, Inc.).

For the liver, the following treatment was performed. First, 0.5 g of the liver was homogenized in 2.5 mL of a 1.15 mass % potassium chloride (KCl) solution, and put in an ice-cooled test tube. Further, the test tube was centrifuged (gravitational acceleration: 9830 G, 10 min, 4° C.), and the supernatant thereof was taken as a coarse enzyme liquid. Subsequently, for the coarse enzyme liquid, the intensity of fatty acid synthetase (FAS) activity was determined by measuring enzyme activity (wavelength: 340 nm) from the rate of decline of NAPDH in the presence of 100 μM malonyl-CoA and 25 μM acetyl CoA in accordance with methods described in Nepokroeff et al., (Methods Enzymol, 35: 37-44, 1975) and Kelley et al., (Biochem. J, 235: 87-90, 1986). Further, for the coarse enzyme liquid, the intensity of fatty acid degrading enzyme (carnitine palmitoyltransferase: CPT) was determined by measuring enzyme activity (wavelength: 412 nm) from the reaction rate of dithionitrobenzoic acid (DTNB) in the presence of 2 mM palmitoyl CoA and 125 mM L-carnitine in accordance with a method described in Markwell et al., (J Biol. Chem, 248: 3426-3432, 1973). FIGS. 13 to 22 show the results. For significant differences between the groups (A to F groups) in FIGS. 13 to 22, a Tukey HSD multiple comparison test was conducted, and $P<0.05$ was determined as being statistically significant.

Discussion

Figure 13:
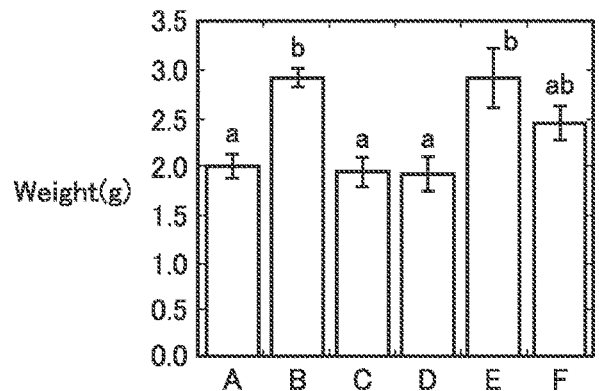
FIG. 13 is a graph showing the body weights of the mice of the groups in the eighth test.

FIG. 13 is a graph showing the body weights of the mice of the groups in the eighth test. From FIG. 13, it is understood that body weight increase in the B group, the E group and the F group cannot be inhibited as compared to that in the A group, and body weight increase in the C group and the D group is significantly inhibited as compared to that in the A group.

Figure 14:
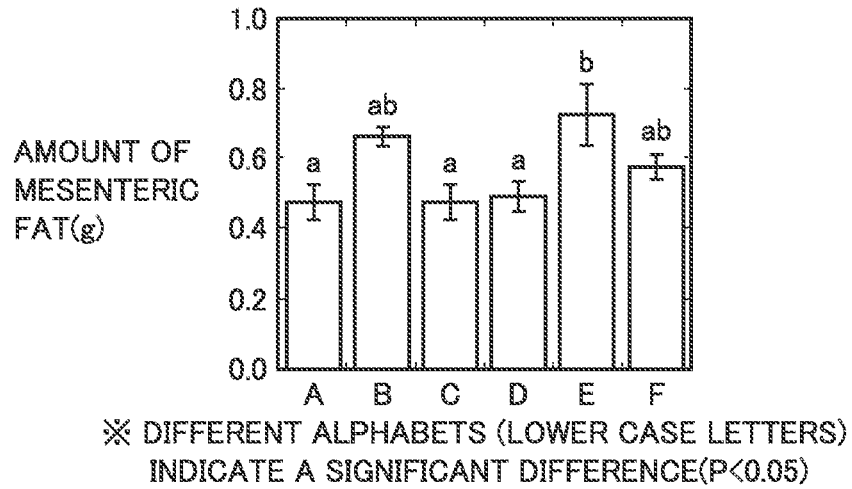
FIG. 14 is a graph showing the amounts of mesenteric fat in the mice of the groups in the eighth test.
Figure 15:
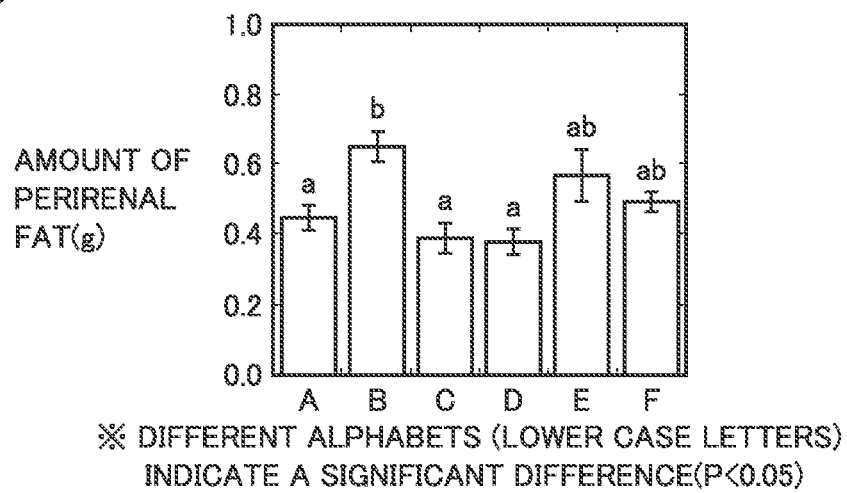
FIG. 15 is a graph showing the amounts of perirenal fat in the mice of the groups in the eighth test.
Figure 16:
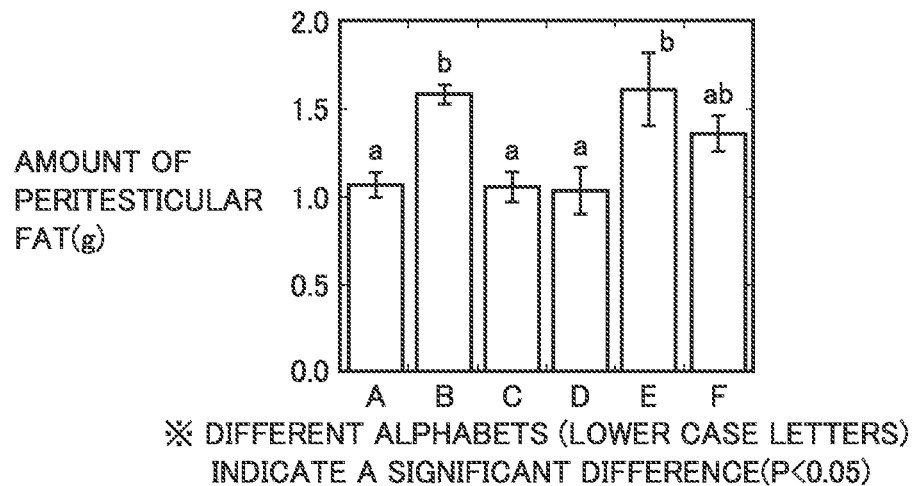
FIG. 16 is a graph showing the amounts of peritesticular fat in the mice of the groups in the eighth test.
Figure 17:
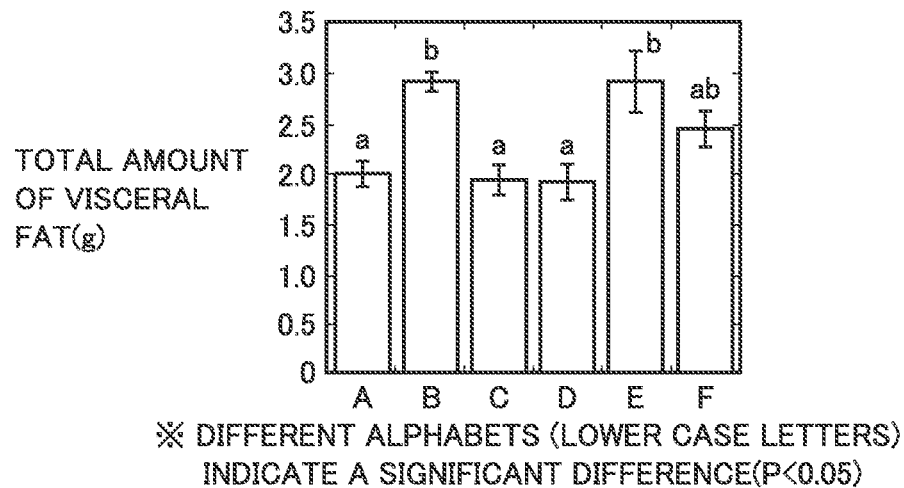
FIG. 17 is a graph showing the total amounts of visceral fat in the mice of the groups in the eighth test.

FIG. 14 is a graph showing the amounts of mesenteric fat in the mice of the groups in the eighth test. FIG. 15 is a graph showing the amounts of perirenal fat in the mice of the groups in the eighth test. FIG. 16 is a graph showing the amounts of peritesticular fat in the mice of the groups in the eighth test. FIG. 17 is a graph showing the total amounts of visceral fat in the mice of the groups in the eighth test. From FIGS. 14 to 17, it is evaluated that fat accumulation in the organs in the C group and the D group is or tends to be significantly inhibited as compared to that in the B group, the E group and the F group. Accordingly, suggested that in the C group and the D group, a visceral fat accumulation inhibiting effect is obtained in loading of fructose.

Figure 18:
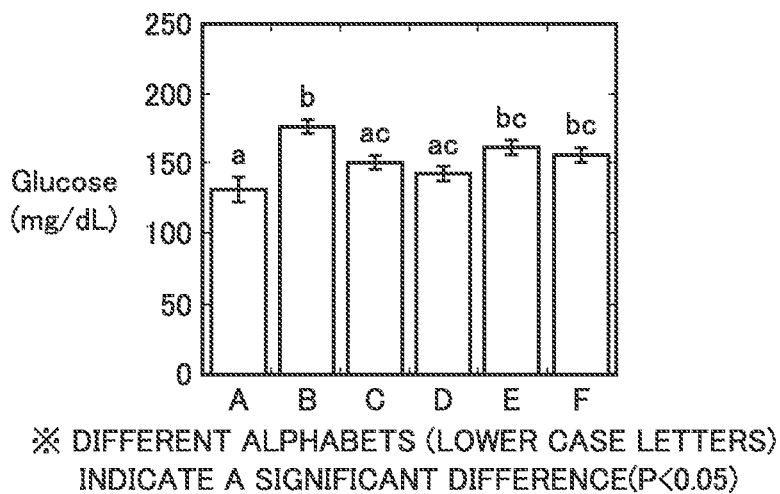
FIG. 18 is a graph showing blood glucose levels in the serum of the mice of the groups in the eighth test.
Figure 19:
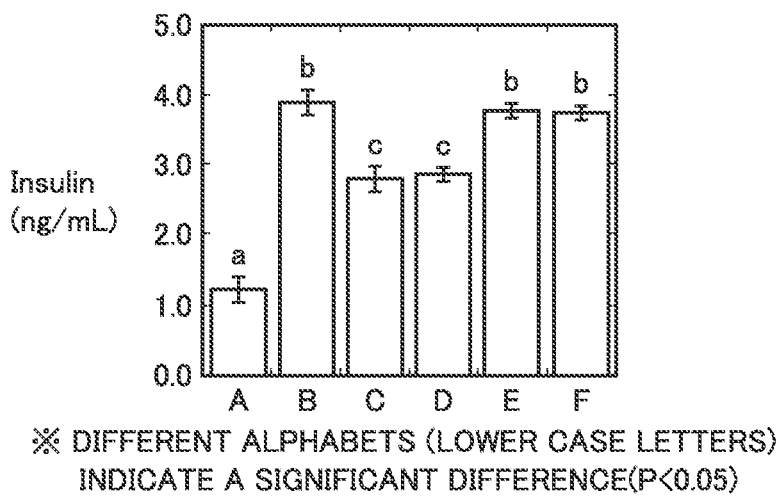
FIG. 19 is a graph showing the amounts of insulin in the serum of the mice of the groups in the eighth test.

FIG. 18 is a graph showing blood glucose levels in the serum of the mice of the groups in the eighth test. FIG. 19 is a graph showing the amounts of insulin in the serum of the mice of the groups in the eighth test. FIG. 18 indicates that the glucose level in the C group and the D group is significantly lower as compared to that in the B group. Further, FIG. 19 indicates that the amount of insulin in the C group and the D group is significantly lower as compared to that in the E group and the F group.

Figure 20:
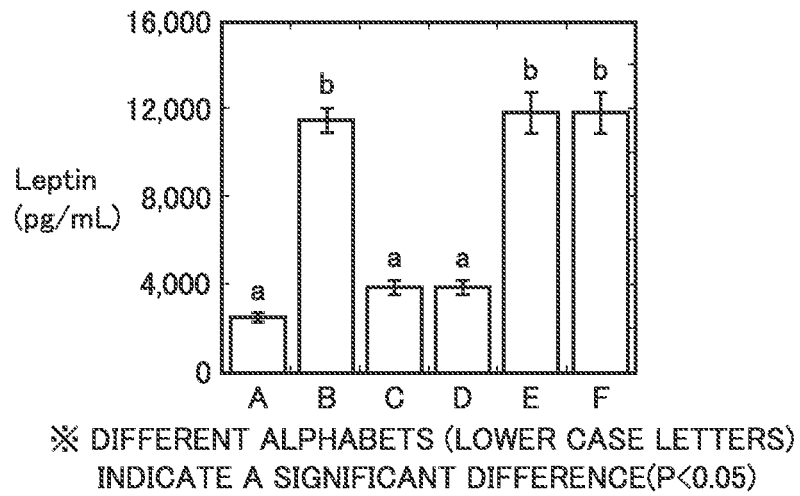
FIG. 20 is a graph showing the concentrations of leptin in the serum of the mice of the groups in the eighth test.

FIG. 20 is a graph showing the concentrations of leptin in the serum of the mice of the groups in the eighth test. FIG. 20 indicates that in the C group and the D group, the amount of production of leptin in a biological body decreases, and therefore a visceral fat accumulating inhibiting effect is obtained even when fructose is loaded.

Figure 21:
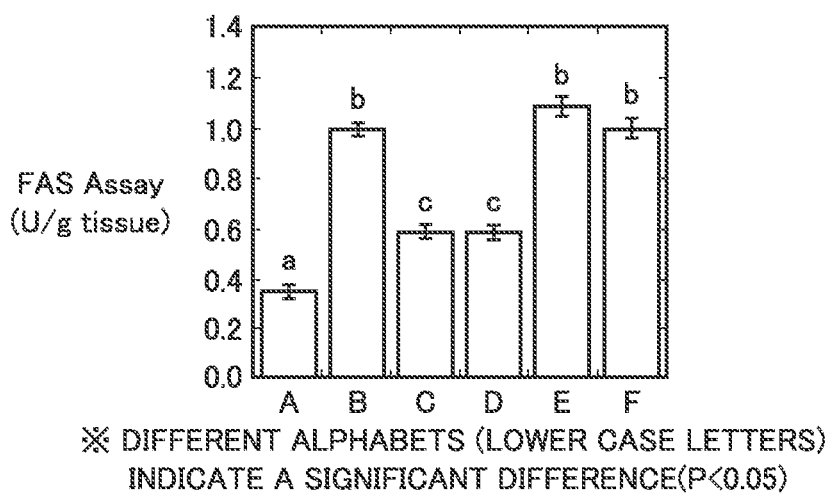
FIG. 21 is a graph showing the intensities of hepatic FAS activity in the mice of the groups in the eighth test.
Figure 22:
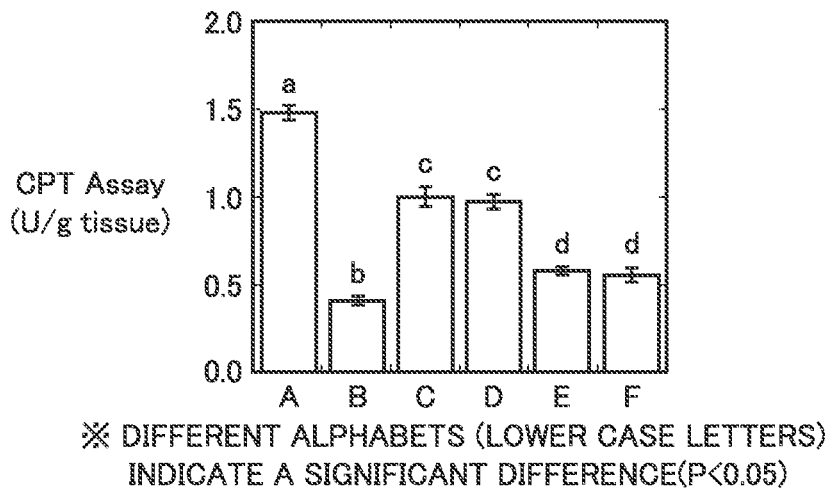
FIG. 22 is a graph showing the intensities of hepatic CPT activity in the mice of the groups in the eighth test.

FIG. 21 is a graph showing the intensities of hepatic FAS activity in the mice of the groups in the eighth test. From FIG. 21, it is evaluated synthesis of fatty acids in the C group and the D group is significantly inhibited as compared to that in the B group, the E group and the F group. Accordingly, it is suggested that in the C group and the D group, synthesis of fatty acids is inhibited, and therefore a visceral fat accumulating inhibiting effect is obtained in loading of fructose. Further, FIG. 22 is a graph showing the intensities of hepatic CPT activity in the mice of the groups in the eighth test. From FIG. 22, it is evaluated that decomposition of fatty acids in the C group and the D group is significantly promoted as compared to that in the B group, the E group and the F group. Accordingly, it is suggested that in the C group and the D group, decomposition of fatty acids is promoted, and therefore a visceral fat accumulating inhibiting effect is obtained in loading of fructose.

Ninth Test

By administering the biological function regulating agent of sample 3 to Hos: HR-1 mice suitable for observing a change in the skin, a test was conducted on whether or not the biological function regulating agent had a skin metabolism promoting action. Specifically, the ninth test was conducted in the following procedure.

Test Method 15 seven-week-old female Hos: HR-1 mice were provided by purchase from Hoshino Laboratory Animals, Inc., and the mice were reared up to eight weeks of age. Thereafter, the mice were divided into three groups: a X group to be given a Labo MR Stock feed (manufactured by Nosan Corporation) as normal food and water, a Y group to be given a purified feed for HR-AD and water and a Z group to be given a purified feed for HR-AD with the biological function regulating agent of sample 3 added at 5 mass % and water, where each group had five mice (n=5). Thereafter, a relevant feed and water were given to the mice of each group for 8 weeks (56 days) to rear the mice. During rearing, the amount of feed intake and body weight in each mouse were measured and photographing was performed once a week. Further, mice to be euthanized before the start of rearing and at the end of rearing were selected from the mice of each group, and the skin of the dorsal part and the abdominal part (lumbar part) of each of the euthanized mice was collected. Further, H. E. stained samples of the skin were prepared to make a histopathological observation including measurement of the thickness of the keratinous layer of the skin, etc. Table 13 shows the thickness of the keratinous layer of the skin which was measured at each of the dorsal parts (neck dorsal and center of dorsal part) and the abdominal part (lumbar part) of each of the mice. The purified feed for HR-AD is a feed that enables evaluation of atopic dermatitis because an atopic dermatitis (AD)-like symptom is caused by deficiency of polyvalent unsaturated fatty acids (n-6 PUFAs). For its composition, the feed contains arginine at 0.75 mass %, histidine at 0.60 mass %, isoleucine at 1.03 mass %, leucin at 2.02 mass %, lysine at 1.69 mass %, methionine at 0.69 mass %, tyrosine at 1.17 mass %, alanine at 0.62 mass %, proline at 2.32 mass %, phenylalanine at 1.03 mass %, tryptophane at 0.07 mass %, valine at 1.27 mass %, cysteine at 0.08 mass %, glycine at 0.39 mass %, threonine at 0.87 mass %, serine at 1.18 mass %, aspartic acid at 1.47 mass % and glutamic acid at 4.74 mass % as amino acids; vitamin A 32157 IU, vitamin D3 4799 IU, 160 mg of vitamin E, 5 mg of vitamin K, 868.2 mg of choline, 0.09 mg of folic acid, 320 mg of niacin, 0.8 mg of biotin, 13 mg of vitamin B1, 16.3 mg of vitamin B2, 52.7 mg of vitamin B6, 0.08 mg of vitamin B12, 129.6 mg of vitamin C and 29.7 mg of pantothenic acid per kg as vitamins; and calcium at 0.9 mass %, chlorine at 0.33 mass %, magnesium at 0.02 mass %, phosphorus at 0.77 mass %, potassium at 0.42 mass %, sodium at 0.2 mass %, selenium at 0.00 mass %, iodine at 0.22 mg/kg, iron at 276.78 mg/kg, cobalt at 0.002 mass %, manganese at 79.28 mg/kg, zinc at 122.52 mg/kg and copper at 21.50 mg/kg as minerals. In Table 13, "Mean" denotes a median value, and "S.D." denotes a standard deviation.

TABLE 13

| Group | Feed | | Dorsal part of neck | Center of dorsal part | Lumbar part | Average for three parts |
|---|---|---|---|---|---|---|
| X | Labo MR Stock | n | 5 | 5 | 5 | 5 |
| | | Mean | 9.35 | 11.24 | 10.06 | 10.22 |
| | | S.D. | 1.55 | 1.04 | 1.83 | 1.40 |
| Y | Purified feed for HR-AD | n | 5 | 5 | 5 | 5 |
| | | Mean | 20.28** | 22.78$ | 21.61$ | 21.56$$ |
| | | S.D. | 4.20 | 5.79 | 7.27 | 5.28 |
| Z | Purified feed for HR-AD + FCP-3 | n | 5 | 5 | 5 | 5 |
| | | Mean | 14.34+ | 17.68 | 20.82 | 17.62 |
| | | S.D. | 2.00 | 2.33 | 3.00 | 2.34 |

**p <0.01 Student's t-test vs Standard Diet group
$p <0.05 $$: p <0.01 Welch's t-test vs Standard Diet group
+p <0.05 ++: p <0.01 Dunnett's test vs HR-AD Diet group Discussion First, in the Y group, the skin of the dorsal part (neck dorsal part and center of dorsal part) and the abdominal part (lumbar part) was desquamated, and the thickness of the keratinous layer significantly increased. This revealed that the mice of the Y group were established as an atopic dermatitis-like model with a dried skin and a thickened epidermis. On the other hand, in the Z group, the dried state of the skin was less changed as compared to that in the Y group, but as shown in Table 13, the value of the thickness of the keratinous layer of the neck dorsal part was significantly low, so that it was considered that thickening of the epidermis was inhibited under the skin metabolism promoting action of the biological function regulating agent.

Tenth Test

By giving biological function regulating agent of sample 4 to healthy men and women aged 20 or older and 70 or younger, a test was conducted on whether or not the biological function regulating agent had a fat accumulating inhibiting action on humans. Specifically, the tenth test was conducted in accordance with the following procedure.

Test Method

This test was conducted in compliance with the program for practice of this test with consideration given to "Helsinki Declaration (Version with added notes in Tokyo in 2004)" and "Ethical Guideline for Epidemiological Research" (Ministry of Education, Culture, Sports, Science and Technology/Ministry of Health, Labor and Welfare Notification No. 1 in 2004)". The protocol of this test was approved by an ethical review board (approval No: RCB 2020-001-02), and registered in UMIN (UMIN 000040736). In this test, a randomized, double-blind placebo-controlled parallel intergroup test was conducted after written agreements were obtained from subjects. In this test, a total of three measurements were made, i.e. measurements were made at a time point of screening assignment, at a time point before intake (0 time) and at a time point when a test food was given in an absolute dry amount of 5.0 g a day for three months. In one measurement period, one-week adjustment period was provided. Details of the test are described below.

1) Subject Selection Criteria

In accordance with the above-described protocol, persons falling under the following criteria were selected: i) men and women aged 20 or older and 70 or younger; ii) healthy persons having no abnormality found in physical examination within one year before the start of the test; iii) persons having an initial visceral fat area of 80 cm$^2$ or more; and iv) persons able to maintain an intake ratio of 80% or more for the next six months. Persons falling under the following criteria were excluded: A) persons having a history of heavy disease; B) persons showing an abnormal level in any of hepatic function and renal function tests in physical examination; C) persons showing a disorder in the cardiopulmonary function; D) persons with any of food and drug allergies; E) persons having a surgery of the digestive tract; F) persons diagnosed as having chronic or acute infection by a doctor; G) persons participating in another clinical test at the time of start of this test; H) persons doing vigorous sports and persons on a diet; I) pregnant women; and J) other persons deemed inappropriate by a test director or a person responsible for the test.

2) Assignment of Subjects

Among 109 persons who agreed to participate in this test, 55 persons were engaged in this test in accordance with enrollment criteria. The test directing doctor prepared a stratified random assignment list using random numbers while making sure not to cause imbalance in the visceral fat area during screening between the groups, and sealed the list. The assignment list was provided to only a person responsible for management of test food. Test food described later was distributed to the 55 test participants. Those subject to blinding were all the staff of the test practice organization including an organizer, the test directing doctor, test practitioners and the person responsible for management of test food, and members constituting the ethical review board. The assignment list was unsealed by a person responsible for statistical analysis after the end of the test.

3) Test Food

As test foods, samples 101 (CP group) and sample 4 (FCP group) were used. As a control food (PL group (placebo group)), maltodextrin (trade name: "Pinedex #2" manufactured by Matsutani Chemical Industry Co., Ltd.) was used.

4) Intake Method

The test foods and the control food were each put in an aluminum pouch, and distributed in such a manner the contents thereof were not known. The test participants (subjects) were allowed to take in a relevant food (5.0 g/day) on their own time for three months. The test participants were instructed to eat the food before the end of the day with limits of not more than one packet (5.0 g) per day in case of failing to take in the food.

5) Evaluation Items

5-1) Test Schedule

Various measurements were made before intake (0 time) and at three months of intake (3 months), and a measured value at each time point and an amount of change from that at 0 time were used as outcomes.

5-2) Measurement of Visceral Fat Area

The visceral fat area was measured using Dualscan HDS-2000 (manufactured by OMRON Corporation, medical equipment approval No: 22300 BZX 00104000). The Dualscan HDS-2000 is a visceral fat measuring apparatus capable of easily and safely calculating a visceral fat area by employing dual impedance method, where it is possible to identify visceral fat and abdominal subcutaneous fat by feeding an electric current through two pathways and non-invasively measure the visceral fat area without risk of exposure.

5-3) Measurement of Skin Quality

Measurement of skin quality was performed only on subjects who agreed to photograph their faces. The measurement was performed after the subjects were conditioned at room temperature 20 minutes or longer after only face-wash for men and cleansing and face-wash for women. The measurement was performed with Roboskin Analyzer (manufactured by Shibuya Kogyo Co., Ltd.). Specifically, the face was photographed in the frontal direction, in the rightward direction and in the leftward direction, pigmentation was evaluated by the algorism of Roboskin Analyzer.

6) Statistical Analysis

Statistical analysis was performed using STATMATEV (manufactured by ATOMS) for Windows (registered trademark). All the statistical analyses were performed by a two-tailed test, and the level of significant difference was set to 5% in a confidence interval of 95%. A Wilcoxon signed ranks test was conducted for intragroup comparison before and after intake. A Mann-Whitney U test was conducted for intergroup comparison between two groups: FCP group and PL group; and CP group and PL group. A one-way Anova test was conducted for intergroup comparison among three groups: FCP group, PL group and CP group, and a two-tailed test in the Turkey test was conducted as a posterior test to calculate a significant difference. Table 14 shows changes in visceral fat area, and Table 15 shows the results of skin quality (evaluation on increased or decreased pigmentation).

TABLE 14

|  |  | N number | 0 time | N number | 3 months | Δ |
|---|---|---|---|---|---|---|
| CP group | Total | 19 | 111.68 ± 32.68 | 17 | 116.12 ± 28.19 | 1.3588 ± 25.25 |
|  | Men of less than 110 cm² | 9 | 85.378 ± 13.36 | 7 | 97.771 ± 22.32 | 12.429 ± 28.56 |
|  | Men of 110 cm² or more | 9 | 140.88 ± 21.37 | 9 | 134.58 ± 18.80 | −6.3 ± 20.20 |
| FCP group | Total | 19 | 114.34 ± 29.34 | 16 | 105.08 ± 23.78 # | −7.163 ± 19.69 |
|  | Men of less than 110 cm² | 7 | 90.771 ± 11.63 | 7 | 94.029 ± 28.90 | 3.2571 ± 18.62 |
|  | Men of 110 cm² or more | 10 | 136.06 ± 21.67 | 8 | 115.15 ± 13.79 $$## | −16.48 ± 17.03 |
| PL group | Total | 17 | 111.82 ± 39.59 | 15 | 115.79 ± 29.34 | −2.307 ± 21.78 |
|  | Men of less than 110 cm² | 8 | 93.788 ± 11.59 | 8 | 103.81 ± 18.18 | 10.025 ± 14.60 |
|  | Men of 110 cm² or more | 4 | 153.85 ± 30.07 | 4 | 145.98 ± 22.23 | −7.875 ± 11.86 |

Average ± Standard Deviation
Intragroup comparison: Mann-Whitney U test, $ P <0.05, $$ P <0.01 (VS PL group)
Intergroup comparison: Wilcocson Singed-Ranks Test, # P <0.05, ## P <0.01 (VS 0 time)

TABLE 15

|  |  | N number | 0 time | N number | 3 months | Δ |
|---|---|---|---|---|---|---|
| CP group | Pigmented patches (number LV 2.) | 14 | 13.07 ± 7.89 | 12 | 11.08 ± 7.29 | −2.58 ± 6.03 |
|  | Pigmented patches (area LV 3.) | 14 | 30.43 ± 47.51 | 12 | 6.25 ± 5.57 # | −14.00 ± 28.30 |
|  | Pigmented patches (area LV 2.) | 14 | 127.71 ± 94.73**$ | 12 | 101.83 ± 93.32 | −31.58 ± 91.68 *$$ |
| FCP group | Pigmented patches (number LV 2.) | 15 | 8.47 ± 6.74 | 13 | 5.92 ± 3.67 $$ | −1.77 ± 4.99 $$ |
|  | Pigmented patches (area LV 3.) | 15 | 9.20 ± 10.84 | 13 | 7.69 ± 8.47 $$ | −0.92 ± 10.39 $$ |
|  | Pigmented patches (area LV 2.) | 15 | 37.07 ± 45.21 | 13 | 37.77 ± 35.65 $$ | 10.38 ± 31.91 $$ |
| PL group | Pigmented patches (number LV 2.) | 15 | 9.87 ± 5.58 | 13 | 11.00 ± 7.83 | 0.23 ± 4.46 |
|  | Pigmented patches (area LV 3.) | 15 | 10.00 ± 9.55 | 13 | 30.38 ± 75.42 | 19.46 ± 75.37 |
|  | Pigmented patches (area LV 2.) | 15 | 48.40 ± 32.37 | 13 | 127.31 ± 138.27 | 73.15 ± 125.19 |

Average ± Standard Deviation
Intragroup comparison: Mann-Whitney U test, $ P <0.05, $$ P <0.01 (VS PL group)
Intergroup comparison: Wilcocson Singed-Ranks Test, # P <0.05, ## P <0.01 (VS 0 time)
Intragroup comparison: Tukey test by ANOVA, * P <0.05, **P <0.01 (VS PL group)

Discussion

Table 14 reveals that there was no significant difference in visceral fat area between the CP group and the PL group and 0 time. However, there was a significant difference between the FCP group and the 0 time. In the stratified groups of men of 110 cm² or more, the FCP group had a significantly smaller visceral fat area as compared to the PL group. For skin quality (evaluation on increased or decreased pigmentation), the FCP group had a significantly smaller area and number as compared to the PL group. The FCP group also had significantly smaller Δ (3 month—0 time) as compared to the PL group. Table 15 reveals that for skin quality (evaluation on increased or decreased pigmentation), the CP group had significantly smaller Δ (3 month—0 time) as compared to the PL group.

Seven of the subjects dropped out because of being unable to visit the hospital due to inevitable reasons in measurement of the third month. For subjects other than the dropouts, intake of the test food did not cause an adverse event. From the above, it was suggested that intake of the biological function regulating agent of sample 4 at a dose of 5.0 g per day for three months was safe, and intake of the biological function regulating agent reduced the visceral fat area in healthy men having a visceral fat area of 110 cm² or more. The reason why the subjects having a visceral fat area of 110 cm² or more showed a significant difference may be that the subjects had a larger amount of visceral fat as compared to persons of less than 110 cm², and thus had visceral fat easily combusted by intake of the biological function regulating agent, so that a difference was likely to occur in three months. Thus, it is considered that even persons having a visceral fat area of less than 110 cm² may obtain a similar effect by continuing intake of the biological function regulating agent. It is suggested that intake of the biological function regulating agent not only reduces the visceral fat area but also inhibits pigmentation on the skin.

Eleventh Test

By adding the biological function regulating agent of sample 5 to fat cells differentiated from mouse-derived precursor fat cells (3T3-L1, passage number: 7 passages, 13 PDL), a test was conducted on whether or not the biological function regulating agent of sample 5 had a fat accumulation inhibiting action. Specifically, the eleventh test was conducted in accordance with the following procedure.

Test Method

The eleventh test was conducted in the same manner as in the third test except that the sample added to the fat cells was changed to sample 5. Table 16 shows the results.

TABLE 16

| | | Blank = 100 | | VS Blank | |
|---|---|---|---|---|---|
| Sample | Final conc. | Ave | Standard deviation | Tukey test | Assessment |
| Blank | — | 100 | 6.215 | — | — |
| Berberine chloride | 2 ug/mL | 60 | 2.824 | 0.001 | ** |
| Sample 5 | 0.1 mass % | 80 | 2.932 | 0.015 | * |

Discussion

The results of this test and the third test reveal that sample 5 had a fat accumulation inhibiting effect similarly to samples 1 and 2. This reveals that similar effects are obtained from different raw materials.

Conclusion

From the above, it is understood that the biological function regulating agents of samples 1 to 5 and samples 41 to 49 have a fat accumulation inhibiting action and an epidermal metabolism promoting action. Further, it is indicated that samples 1 to 5 and samples 41 to 49 also have an action of regulating the amount of adipocytokine in a biological body.

The embodiments and Examples disclosed herein are illustrative in every respect, and should not be construed as being limiting. The scope of the present invention is given not by the above description but by claims, and is intended to include all changes within the meaning and limit equivalent to those of claims.

The invention claimed is:

1. A biological function regulating agent comprising a fermented collagen peptide,
the fermented collagen peptide having at least one action selected from the group consisting of an epidermal metabolism promoting action, a fat accumulation inhibiting action, a fat decomposition promoting action and an action of regulating the amount of adipocytokine in a biological body.

2. The biological function regulating agent according to claim 1, wherein the fermented collagen peptide comprises a collagen peptide, and at least one first compound selected from the group consisting of isovaleric aldehyde, 1-octen-3-ol, phenylacetaldehyde and methional.

3. The biological function regulating agent according to claim 1, wherein the fermented collagen peptide comprises a collagen peptide, and at least three first compounds selected from the group consisting of isovaleric aldehyde, 1-octen-3-ol, phenylacetaldehyde and methional.

4. An epidermal metabolism promoting agent, comprising the biological function regulating agent according to claim 1.

5. A fat accumulation inhibiting agent, comprising the biological function regulating agent according to claim 1.

6. An adiponectin production promoting agent, comprising the biological function regulating agent according to claim 1.

7. A fat decomposition promoting agent, comprising the biological function regulating agent according to claim 1.

8. A functional food, comprising the biological function regulating agent according to claim 1.

9. A cosmetic product, comprising the biological function regulating agent according to claim 1.

10. A method for producing a biological function regulating agent comprising a fermented collagen peptide, the method comprising:
providing koji containing koji mold, and a collagen raw material; and
fermenting the collagen raw material with the koji to obtain a biological function regulating agent comprising the fermented collagen peptide, wherein
the bacterial type of the koji mold is a bacterial type belonging to Aspergillus, and
the collagen raw material is at least any of at least one selected from the group consisting of the following first to sixth groups, collagen extracted from at least one selected from the group, gelatin obtained by treating the collagen, and a gelatin degradation product obtained by hydrolyzing the gelatin:

First group: group consisting of hide, skin, bone, cartilage and tendon of cattle;
Second group: group consisting of hide, skin, bone, cartilage and tendon of pig;
Third group: group consisting of hide, skin, bone, cartilage and tendon of sheep;
Fourth group: group consisting of hide, skin, bone, cartilage and tendon of chicken;
Fifth group: group consisting of hide, skin, bone, cartilage and tendon of ostrich;
Sixth group: group consisting of bone, skin and scale of fish.

11. A biological function regulating agent, comprising a fermented collagen peptide produced by fermenting a collagen raw material with koji.

* * * * *